(12) United States Patent
Skomski et al.

(10) Patent No.: US 12,227,536 B2
(45) Date of Patent: Feb. 18, 2025

(54) CRYSTALLINE FORMS OF AN NRTTI COMPOUND

(71) Applicant: Merck Sharp & Dohme LLC, Rahway, NJ (US)

(72) Inventors: Daniel Skomski, East Brunswick, NJ (US); Yongchao Su, Chalfont, PA (US); Wei Xu, North Wales, NJ (US); Marko Cubrovic, Ridgewood, NJ (US); Stephanie Elizabeth Barrett, Cranford, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 768 days.

(21) Appl. No.: 17/415,570

(22) PCT Filed: Dec. 16, 2019

(86) PCT No.: PCT/US2019/066436
§ 371 (c)(1),
(2) Date: Jun. 17, 2021

(87) PCT Pub. No.: WO2020/131649
PCT Pub. Date: Jun. 25, 2020

(65) Prior Publication Data
US 2022/0056067 A1     Feb. 24, 2022

Related U.S. Application Data

(60) Provisional application No. 62/782,549, filed on Dec. 20, 2018.

(51) Int. Cl.
*C07H 19/173* (2006.01)
(52) U.S. Cl.
CPC ........ *C07H 19/173* (2013.01); *C07B 2200/13* (2013.01)
(58) Field of Classification Search
CPC .... C07B 220/13; C07H 19/173; C07H 19/16; A61K 31/7076
USPC .......................................................... 514/46
See application file for complete search history.

(56) References Cited

U.S. PATENT DOCUMENTS

| | | | |
|---|---|---|---|
| 6,333,315 B1 | 12/2001 | Ohrui et al. | |
| 6,825,331 B2 | 11/2004 | Manoharan et al. | |
| 7,339,053 B2 * | 3/2008 | Kohgo | A61P 43/00 536/27.61 |
| 8,673,912 B2 | 3/2014 | Cannon et al. | |
| 8,771,744 B2 | 7/2014 | Ruecroft et al. | |
| 2014/0343102 A1 | 11/2014 | Sutton et al. | |
| 2017/0342053 A1 | 11/2017 | Lee et al. | |
| 2019/0388336 A1 | 12/2019 | Barrett et al. | |
| 2019/0388590 A1 | 12/2019 | Barrett et al. | |

FOREIGN PATENT DOCUMENTS

| | | |
|---|---|---|
| WO | 2015164479 A1 | 10/2015 |
| WO | 2017053216 A2 | 3/2017 |

OTHER PUBLICATIONS

Rouhi, Chemical & Engineering News, 2003, 81(8), 32-35.*
Brittain, Polymorphism in Pharmaceutical Solids-Drugs and The Pharmaceutical Sciences, 1999, 95, p. 236.*
Hirayama, Noriaki, Handbook for Fabrication of Organic Compound Crystals, Handbook for Fabrication of Organic Compound Crystals, N/A, 3 pages, 2008, Kodansha.
Caira, Crystalline Polymorphism of organic compounds, Topics in Current Chemistry, 1998, 163-208, 198.
Bernstein, J., Bioavailability, Polymorphism of molecular crystals, 2007, 324-330 (translated pp. 1-9), Ch. 7.3.2.
Byrn, Stephen, et al., Pharmaceutical Solids: A Strategic Approach to Regulatory Considerations, Pharmaceutical Research, 1995, p. 945-954, vol. 12, No. 7.
Kummerer, K., Pharmaceuticals in the environment, Annual Review of Environment and Resources, 2010, 57-75, 35.
Kuznetsova, G.A., Methodological instructions, Irkutsk State University (Seihveisu), Department of General Physics, 2005, 1, N/A.
Sharma, Anamika et al., Polymorphism in Pharmaceutical Compounds, Proceeding of National Conference on Advancements and Futuristic Trends in Material Science, 2011, 39-48, N/A.
Variankaval, Narayan et al., From Form to Function: Crystallization of Active Pharmaceutical Ingredients, AIChE Journal, 2008, 1682-1688, 54(7).
CDC, Today's HIV/AIDS Epidemic, Center for Disease Control and Prevention, 2015, 1-4, N/A.
Chemburkar, Sanjay R. et al., Dealing with the Impact of Ritonavir Polymorphs on the Late Stages of Bulk Drug Process Development, Organic Process Research & Development, 2000, 413-417, 4.
Hattori, S., et al, "Potent Activity Of A Nucleoside Reverse Transcriptase Inhibitor", Antimicrobial Agents and Chemotherapy, 2009, pp. 3887-3893, vol. 53.
International Search Report for PCT/US2019/066436, mailed Feb. 24, 2020; 20 pages.
Kawamoto, A., et al, "2'-Deoxy-4'-C-Ethynyl-2-Halo-Adenosines Active Against Drug-Resistant Human Immunodeficiency Virus 1 Variants", Interational Journal of Biochemistry Cell Biology, 2008, pp. 2410-2420, vol. 40, No. 11.
Michailidis, E., et al, "4'-Ethynyl-2-Fluoro-2'-Deoxyadenosine (EFdA) Inhibits HIV-1 Reverse Transcriptase With Multiple Mechanisms", Journal of Biological Chemistry, 2014, pp. 24533-24548, vol. 289, No. 35.
Michailidis, E., et al, "Mechanism Of Inhibition Of HIV-1 Transcriptase By 4'-Ethynyl-2-Fluoro-2'-Deoxyadenosine Triphosphate, A Translocation-Defective reverse Transcriptase Ihibitor", Journal of Biological Chemistry, 2009, pp. 35681-35691, vol. 284, No. 51.

(Continued)

*Primary Examiner* — Ganapathy Krishnan
(74) *Attorney, Agent, or Firm* — Eric Greenwald; John C. Todaro

(57) ABSTRACT

The present disclosure provides novel anhydrate crystalline Forms 1 and 4 of 4'-Ethynyl-2-fluoro-2'-deoxyadenosine and pharmaceutical compositions thereof, each of which may be useful for the inhibition of HIV reverse transcriptase, the treatment or prophylaxis of HIV infection and/or the treatment, prophylaxis and/or delay in the onset or progression of AIDS or ARC.

18 Claims, 16 Drawing Sheets

(56) References Cited

OTHER PUBLICATIONS

Ohrui, H., et al, 2'-Deoxy-4'-C-Ethynyl-2-Fluoroadenosine: A Nucleoside, Nucleosides, Nucleotides & Nucleic Acids, 2007, pp. 1543-1546, vol. 26.
Sidibé, Michel (Executive Director), UNAIDS report on the global AIDS epidemic 2013, Joint United Nations Programme on HIV/AIDS (UNAIDS), 2013, 1-198, JC2502/1/E.
Stoddart, C.A., et al, "Oral Administration Of The Nucleoside EFdA (4'-Ethynyl-2-Fluoro-2'-Deoxyadenosine) Provides Rapid Suppression Of HIV Viremia In Humanized Mice And Favorable Pharmacokinetic Properties In Mice And The Rhesus Macaque", Antimicrobial Agents and Chemotherapy, 2015, pp. 4190-4198, vol. 59, No. 7.
Braga, Dario et al., Crystal Polymorphism and Multiple Crystal Forms, Struct Bond, 132, 25-50, 2009.
Hilfiker, Rolf et al., Relevance of Solid-state Properties for Pharmaceutical Products, Polymorphism: in the Pharmaceutical Industry, Chapter 1, 1-19, 2006.

\* cited by examiner

CRYSTALLINE FORMS OF AN NRTTI COMPOUND

CROSS-REFERENCE TO RELATED APPLICATIONS

This application is a National Stage application of International Patent Application No. PCT/US2019/066436, filed Dec. 16, 2019, which claims priority to U.S. Provisional Patent Application No. 62/782,549, filed Dec. 20, 2018.

BACKGROUND OF THE INVENTION

Human immunodeficiency virus (HIV-1) infection is a serious condition which if left untreated ultimately destroys the host's immune system resulting in acquired immunodeficiency syndrome (AIDS) and premature death. Despite advances in antiretroviral therapies (ART), HIV continues to be a global epidemic and a global public health priority. An estimated 35 million people worldwide were living with HIV in 2012 (Global Report: UNAIDS report on the global AIDS epidemic 2013. UNAIDS/JC2502/1/E). In the U.S., an estimated 1.2 million people are living with HIV and about 50,000 become newly infected each year. HIV seropositive individuals are initially asymptomatic but typically develop AIDS related complex (ARC) followed by AIDS. More than 650,000 people in the U.S. have died with AIDS and more than 14,000 additional deaths are reported each year. Treatment can help people with HIV live longer, healthier lives, but currently only 30 percent of people with HIV in the U.S. are successfully keeping their virus under control. (Center for Disease Control and Prevention. Today's HIV/AIDS epidemic. July 2015).

Nucleoside and nucleotide reverse transcriptase inhibitors (NsRTIs and NtRTIs, or collectively NRTIs) inhibit HIV reverse transcriptase and block HIV replication. They are one of 6 classes of HIV antiretrovirals (ARVs) used as components of potent and durable multi-drug regimens that typically combine two NRTIs with a non-nucleoside reverse transcriptase inhibitor, an integrase strand transfer inhibitor, or a protease inhibitor. Combination treatment maximizes treatment response and minimizes the emergence of drug resistance.

Due to the fact that HIV replication is asynchronous, antiretroviral agents need to be continuously present in patients to effectively suppress viremia. For most classes of drugs including protease inhibitors, integrase inhibitors, and non-nucleoside reverse transcriptase inhibitors, efficacy is dictated by circulating drug concentrations and dosing is aimed at providing circulating drug concentrations throughout the dosing interval (i.e. Cmin) that exceed those required to suppress viral replication (i.e. the IC50 or IC95). In contrast, upon entering cells, NRTIs and nucleotide reverse transcriptase inhibitors (NtRTIs such as tenofovir) enter into obligate intracellular anabolic pathways for conversion to active phosphorylated forms, and it is their intracellular half-lives rather than their plasma concentrations that dictate their persistent effect. Currently approved NRTIs are administered at least once-daily.

4'-Ethynyl-2-fluoro-2'-deoxyadenosine (EFdA, also known as MK-8591) is a nucleoside reverse transcriptase translocation inhibitor (NRTTI) that blocks HIV-1 and SIV viral replication in vitro (Kawamoto, A., Kodama, E., Sarafianos S. F. et al, Int. J. Biochem. Cell Biol.; 40(11):2410-20 [2008]; Ohrui, H., Kohgo, S., Hayakawa, H. et al, *Nucleosides, Nucleotides & Nucleic Acids,* 26, 1543-1546 [2007]) and in vivo (Hattori, S., Ide, K., Nakata, H. et al. Antimicrobial. Agents and Chemotherapy, 53, 3887-3893 [2009]).

U.S. Pat. No. 7,339,053 describes EFdA (referred to in the '053 patent as 2'-deoxy-4'-C-ethynyl-2-fluoroadenosine) and a synthesis for making EFdA. EFdA has the following chemical structure:

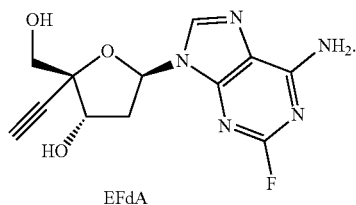 [SMILES: C#C[C@]1(CO)O[C@@H](n2cnc3c(N)nc(F)nc32)C[C@@H]1O]

EFdA

U.S. Pat. No. 7,339,053 describes the use of water as a final crystallization solvent in the synthesis for making EFdA which is understood to produce a monohydrate crystalline form of EFdA.

EFdA is metabolized in cells to their active triphosphate anabolite which inhibits HIV reverse transcriptase. In contrast to NRTIs currently available for the treatment of HIV infection which lack a 3'—OH group to block incorporation of incoming nucleotide, EFdA retains a 3'—OH group and acts as a chain terminator by preventing translocation of the primer:template in the reverse transcriptase (RT) active site and preventing binding of incoming deoxyribonucleotides triphosphates (dNTPs). In addition, the pucker of the modified ribose ring of EFdA is believed to contribute to inhibition of reverse transcriptase by placing the 3'-OH in a vector, in which phosphotransfer from the incoming nucleotide is inefficient. (Michailidis E, et al., Mechanism of inhibition of HIV-1 reverse transcriptase by 4'-ethynyl-2-fluoro-2'-deoxyadenosine triphosphate, J Biol Chem 284: 35681-35691 [2009]; Michailidis E, et al., 4'-Ethynyl-2-fluoro-2'-deoxyadenosine (EFdA) inhibits HIV-1 reverse transcriptase with multiple mechanisms, J Biol Chem 289: 24533-24548 [2014]).

In in vitro HIV replication assays, EFdA is a potent antiretroviral and exhibits comparable antiviral activity against clinical isolates across all subtypes that have been evaluated. It is rapidly anabolized in both lymphoid derived cell lines and in peripheral blood mononuclear cells to the active triphosphate in vitro, and the intracellular half-life of EFdA Triphosphate (EFdA-TP) exceeds 72 hrs. (Stoddart, C. A., Galkina, et al., Oral Administration of the Nucleoside EFdA (4'-Ethynyl-2-Fluoro-2'-Deoxyadenosine) Provides Rapid Suppression of HIV Viremia in Humanized Mice and Favorable Pharmacokinetic Properties in Mice and the Rhesus Macaque, Antimicrob Agents Chemother, 2015 July; 59(7): 4190-4198, Published online 2015 May 4).

Currently available drug treatments for HIV infection work in combination to suppress viremia, keeping the virus under control. HIV drug therapy is life-long and strict adherence to treatment regimens is critical to maintain viral suppression, reduce the risk of drug resistance, and minimize the risk of transmission. Efficacious and safe, well-tolerated drugs that are easy to take with low dosing frequency have the potential to improve a patient's adherence and long-term treatment success. For prophylaxis against HIV infection, the only currently available pre-exposure prophylaxis (PrEP) treatment approved by the U.S. Food and Drug Administration is TRUVADA® (emtricitabine/tenofovir DF) for prophylaxis against HIV infection in uninfected people.

Currently available orally administered anti-retroviral drugs are dosed once-daily. Due to the need for continued circulating drug concentrations, the use of long-acting release drug delivery modalities, such implants, are desirable. Less frequent dosing may help to alleviate both practical challenges and the cumulative psychological impact of taking daily HIV medications. Long-acting antiretroviral therapy may potentially help patients return to a greater sense of normalcy and provide flexibility that could impact the way they live, work, travel, relate to others, and see themselves. Additionally, some patients adapt to and may prefer once-weekly, once-monthly or longer interval administration options such as provided by long-acting parenteral (LAP) administration which can result in improved medication adherence.

It is of value to have additional therapy options for people infected with HIV or at risk of HIV infection, that allow for less frequent drug administration than daily dosing, such as long acting parenteral (LAP) implantable formulations. For LAP implantable drug formulations, the most thermodynamically stable crystalline form of a small molecule pharmaceutical agent is desired to avoid physical form transformations during storage and/or shelf life that could alter the in vivo performance and efficacy of the drug (see, e.g., Chemburkar, et al., Organic Process Research & Development 2000, 4, 413-417). However, when utilizing the known monohydrate crystalline form of EFdA, in-situ recrystallization occurs during hot melt extrusion (HME) formulation processing, which results in conversion of the monohydrate crystalline form of EFdA into a mixture of multiple, thermodynamically disfavored anhydrate phases in the drug product.

SUMMARY OF THE INVENTION

The present application discloses the discovery of novel anhydrate crystalline forms of EFdA, i.e., anhydrate crystalline Form 1 of EFdA and anhydrate crystalline Form 4 of EFdA, which have the requisite physical stability for LAP implantable drug formulations of EFdA.

The present disclosure also provides methods for the inhibition of HIV reverse transcriptase, the treatment of HIV or prophylaxis of infection by HIV, and/or the treatment, prophylaxis, and/or delay in the onset or progression of AIDS or ARC using the anhydrate crystalline Form 1 or Form 4 of EFdA. The present disclosure further provides pharmaceutical compositions of each of said anhydrate crystalline Form 1 and Form 4 of EFdA, and methods for the use of each of said crystal forms. Further embodiments include, but are not limited to, procedures for making each of anhydrate crystalline Forms 1 and 4 of EFdA.

DETAILED DESCRIPTION OF THE INVENTION

Figure 1:
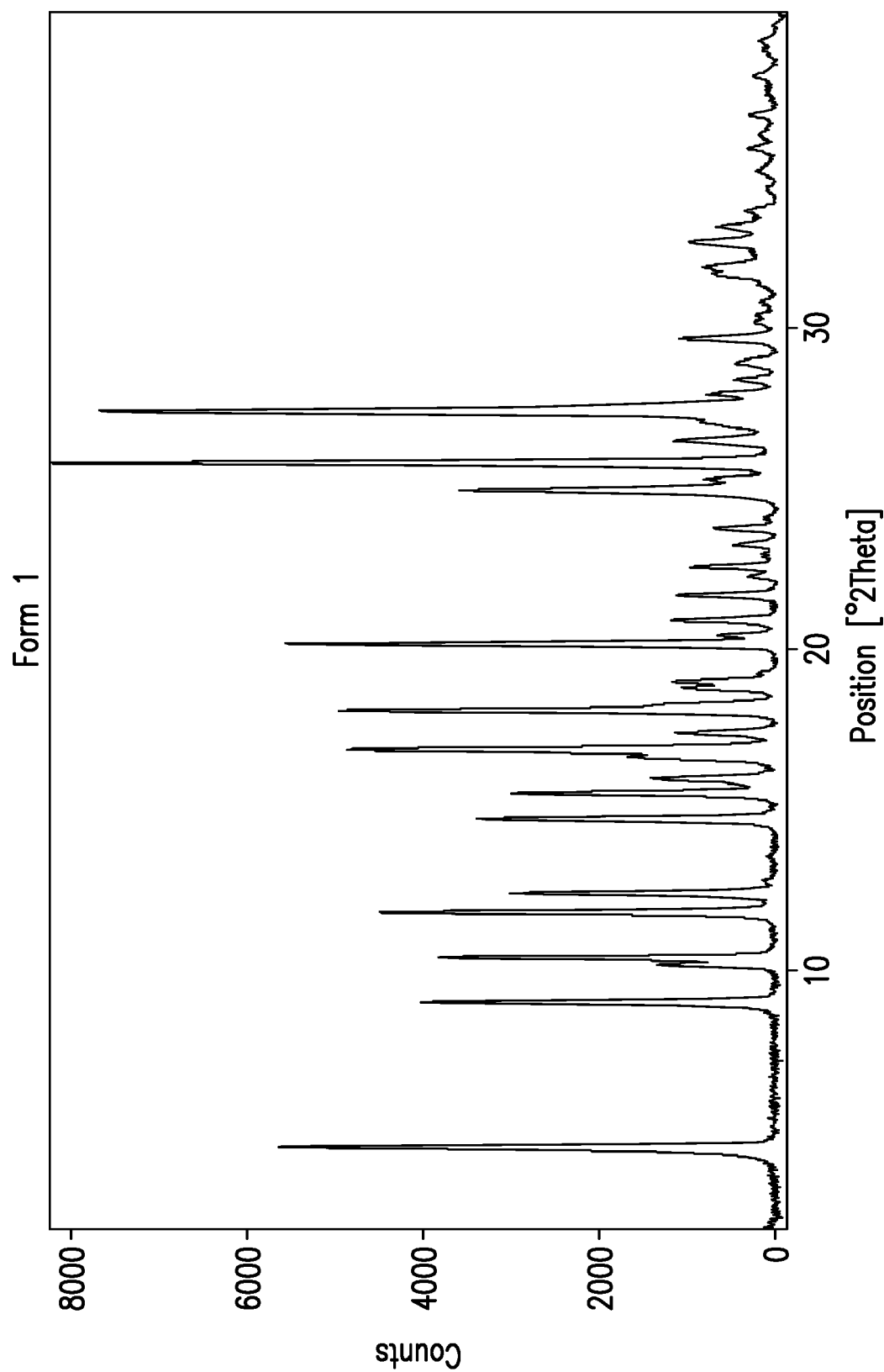
FIG. 1 is a graph of a Powder X-Ray Diffraction ("PXRD") pattern of anhydrate crystalline Form 1 of EFdA, generated using the equipment and methods described herein. The graph plots the intensity of the peaks as defined by counts per second versus the diffraction angle 2 theta (2Θ) in degrees.

The terms used herein have their ordinary meaning and the meaning of such terms is independent at each occurrence thereof. That notwithstanding and except where stated otherwise, the following definitions apply throughout the specification and claims.

"API" means active pharmaceutical ingredient

"FIGURE" may be abbreviated as FIG., Fig. or fig., and refers to the corresponding drawing.

"Patient" or "subject" includes both human and other mammals.

"Mammal" includes humans and other mammalian animals.

"PXRD" refers to powder x-ray diffraction.

"TGA" refers to thermal gravimetric analysis.

"LAP" means long acting parenteral.

"L/D" means length of barrel/diameter of screw.

"s" is seconds.

"Excipient" means an essentially inert substance used as a diluent or to give form or consistency to a formulation.

Anhydrate crystalline Form 1 of EFdA may also be referred to herein as "anhydrate crystalline Form 1," "crystalline Form 1," "anhydrate Form 1" or "Form 1."

Anhydrate crystalline Form 2 of EFdA may also be referred to herein as "anhydrate crystalline Form 2," "crystalline Form 2," "anhydrate Form 2" or "Form 2."

Anhydrate crystalline Form 3 of EFdA may also be referred to herein as "anhydrate crystalline Form 3," "crystalline Form 3," "anhydrate Form 3" or "Form 3."

Anhydrate crystalline Form 4 of EFdA may also be referred to herein as "anhydrate crystalline Form 4," "crystalline Form 4," "anhydrate Form 4" or "Form 4."

Monohydrate crystalline Form MH of EFdA may also be referred to herein as "monohydrate crystalline Form MH," "crystalline Form MH," "monohydrate Form MH" or "Form MK."

The present disclosure provides pharmaceutically acceptable compositions of each of said anhydrate crystalline Form 1 and Form 4 of EFdA.

The term "composition" (or "pharmaceutical composition" or "pharmaceutically acceptable composition") as used herein is intended to encompass a product comprising the specified ingredient(s), and when applicable, the specified amounts, as well as any product which results, directly or indirectly, from combining the specified ingredients. The term is intended to encompass a product comprising one or more active ingredient(s), and the inert ingredient(s), if any, that make up the carrier, as well as any product which results, directly or indirectly, from combination, complexation, or aggregation of any two or more of the ingredients, or from dissociation of one or more of the ingredients, or from other types of reactions or interactions of one or more of the ingredients. The carrier, which may comprise diluent(s) and/or excipient(s), may be any one or more inert ingredients suitable for the delivery mode of the active pharmaceutical ingredient(s), e.g., for oral or parenteral administration, including but not limited to polymer(s) suitable for implantable drug formulations. Accordingly, the pharmaceutical compositions of this disclosure encompass any composition made by admixing Form 1 with Form 2, Form 3 or Form 4, or admixing any mixture of said crystalline forms, and a pharmaceutically acceptable carrier. By "pharmaceutically acceptable" it is meant the carrier must be compatible with the other ingredients of the formulation and not deleterious to the recipient thereof.

The term "composition" (or "pharmaceutical composition" or "pharmaceutically acceptable composition") as used herein is also intended to encompass either the bulk composition and/or individual dosage units. The bulk composition is material that has not yet been formed into individual dosage units. The bulk composition and each individual dosage unit can contain fixed amounts of active agent(s). Non-limiting examples of dosage units include oral dosage units such as tablets, pills and the like and parenteral dosage unit formulations such as implantable dosage units. Similarly, the herein-described method of treating a patient by administering a pharmaceutical composition of the present disclosure is also intended to encompass administration of afore-said bulk composition and individual dosage units.

This present disclosure encompasses methods for the inhibition of HIV reverse transcriptase, for the treatment of HIV or prophylaxis of infection by HIV, and/or the treatment, prophylaxis, and/or delay in the onset or progression of AIDS or ARC, which comprise administering to the subject an effective amount of anhydrate crystalline Form 1 or Form 4 of EFdA. The present disclosure further provides methods for the use of each of said anhydrate crystalline Form 1 and Form 4 of EFdA (1) in the manufacture of a medicament which may be useful (alone or together with additional active ingredients) for the inhibition of HIV reverse transcriptase, for the treatment of HIV or prophylaxis of infection by HIV, and/or the treatment, prophylaxis and/or delay in the onset or progression of AIDS or ARC; and (2) for use in a method for the inhibition of HIV reverse transcriptase, for the treatment of HIV or prophylaxis of infection by HIV, and/or the treatment, prophylaxis and/or delay in the onset or progression of AIDS or ARC. Further embodiments include, but are not limited to, procedures for making each of crystalline Forms 1, 2, 3 and 4 of EFdA.

The discovery of anhydrate crystalline Form 4 of EFdA was unusual and unexpected due to the fact that Form 4 was not found in standard pharmaceutical crystal polymorph screens, but found to be produced as a result of specific processing conditions during HME manufacturing of implantable drug formulations during the course of studies focused on investigating a range of processing conditions for preparing such formulations.

In the following isolation procedures, EFdA monohydrate (Form MH) powder was prepared by organic synthesis and its conversion into anhydrate phases was studied under various conditions. The mononhydrate and anhydrate forms were also investigated in long-acting parenteral HME manufacture.

Isolation of Anhydrate Crystalline Forms 1, 2 and 4 of EFdA By Hot Melt Extrusion (HME) Processing:

Anhydrate crystalline Forms 1, 2, and 4 of EFdA were isolated by hot melt extrusion (HME) processing. Micronized ethylene vinyl acetate (EVA) polymer and monohydrate crystalline Form MH of EFdA were blended with a Turbula T2F mixer at various ratios: 30, 35, 40, 45 and 50 wt % drug. The pre-blend was hot melt extruded with an 18 mm Leistritz twin screw extruder with a 25:1 L/D, throughput of 400 g/hr, temperatures ranging from 100-140° C., feed zone at 40° C., and screw speed at 30 rpm. Two screw configurations were used, both predominately consisting of conveying elements with different mixing sections. The less aggressive screw design contained a mixing section consisting of conveying, kneading elements each 15 mm in length, with twisting angles of 30°, 60°, and 60° ("HME low shear Process A"). The more aggressive screw design included additional mixing segments after the mixing section used in the less aggressive design: conveying, kneading elements each 15 mm in length, with a twisting angle of 90° ("HME high shear Process B"). For both extrusion set-ups, the strands were then air-cooled and pelletized to form micropellets. The pellets were then extruded with a ½" American Kuhne single screw extruder with temperatures ranging from 110-140° C., feed zone at 25° C., and screw speed at 20-25 rpm to form a 2±0.05 mm diameter filament, and then cut to a length of 40±2 mm.

Extrusions performed under the less aggressive HME low shear Process A conditions resulted in formation of a phase mixture of anhydrate Forms 1 and 2 in the extrudate product. Extrusions performed under the more aggressive HME high shear Process B conditions resulted in formation of anhydrate Form 4 in the extrudate product. The formation of the thermodynamically stable anhydrate Form 4 under the aggressive HME high shear Process B processing conditions of the implant drug product and subsequent analytical identification marked the initial discovery of this new phase.

Isolation of Anhydrate Crystalline Forms 1, 2, 3 and 4 of EFdA by Solid-State Powder Differential Scanning calorimetry (DSC) Thermal Processing:

Anhydrate Forms 1, 2, 3 and 4 were isolated by DSC processing. DSC experiments were conducted using a TA Instruments Q2000 with monohydrate Form MH bulk composition in unsealed and hermetically sealed containers. For samples heated in an unsealed DSC pan, 5-10 mg of sample was placed into an aluminum pan and then a lid was placed on top of the pan without sealing the container. For hermetically sealed samples, 5-10 mg were placed into an aluminum pan and then sealed with a hermetic lid. Experiments were normally conducted under non-modulated DSC conditions. Experiments were conducted under a nitrogen stream (50 mL/min).

With thermal processing in an unsealed container, anhydrate Form 3 was generated by heating to 95° C. With further heating to 120° C., anhydrate Form 3 was converted into anhydrate Form 2. These same phases were generated in an unsealed container with varying heating rates (from 0.1° C./min to 75° C./min).

With thermal processing in a hermetically sealed container, anhydrate Forms 1 or 4 were generated. The samples were heated from 20 to 150° C. With a heating rate of 1° C./min, anhydrate Form 4 was generated. With a heating rate of 10° C./min, anhydrate Form 1 was generated.

Physical Characterization of Anhydrate Crystalline Forms 1, 2, 3 and 4 of EFdA

X-ray diffraction (XRD) pattern studies (including powder X-ray diffraction (PXRD) pattern studies), thermogravimetric analysis (TGA), and solid-state NMR (ssNMR) are widely used to characterize molecular structures, crystallinity, and polymorphism and were each used where indicated to characterize Forms 1, 2, 3 and 4 of EFdA. Those skilled in the art will appreciate that a crystalline form of a substance can be further characterized by combinations of measured PXRD values, ssNMR and/or TGA measurements. Thus, in another aspect, crystalline Forms 1, 2, 3, 4 and MH of EFdA can each be characterized by any combination of each of the techniques described herein.

X-Ray Diffraction (XRD) for the EFdA+EVA Implant Compositions: EFdA crystal phase analysis was conducted by X-Ray Diffraction using the Phillips X'Pert PW3040-PRO transmission instrument with a Cu Kα radiation source (λ=1.5418 Å, 45 kv, 40 mA) from 2-40 2θ with scanning step size 0.0167°. The counting time for XRD of the EFdA/EVA extrudate samples was 158.750 seconds.

Powder X-Ray Diffraction (PXRD) for Anhydrate Crystalline Forms 1, 2, 3, 4 and MH: Powder X-ray Diffraction data on the anhydrous polymorphic phases and the Form MH phase of EFdA were acquired on a Panalytical X-pert Pro PW3040 System configured in the Bragg-Brentano configuration and equipped with a Cu radiation source with monochromatization to Kα achieved using a Nickel filter. A fixed slit optical configuration was employed for data acquisition. Data were acquired between 2 and 40° 2θ. Samples were prepared by gently pressing powdered sample onto a shallow cavity zero background silicon holder. The counting time for powder X-Ray Diffraction (PXRD) of EFdA Forms 1, 2, 3, 4 and MH, was 50.800 seconds using EFdA powder samples.

Those skilled in the art will recognize that the measurements of the XRD peak locations for a given crystalline form of the same compound will vary within a margin of error. The margin of error for the 2-theta values measured as described herein is typically +/−0.2° 2-theta. Variability can depend on such factors as the system, methodology, sample, and conditions used for measurement. As will also be appreciated by the skilled crystallographer, the intensities of the various peaks reported in the figures herein may vary due to a number of factors such as orientation effects of crystals in the x-ray beam, the purity of the material being analyzed, and/or the degree of crystallinity of the sample. The skilled crystallographer also will appreciate that measurements using a different wavelength will result in different shifts according to the Bragg-Brentano equation. Such further XRD patterns generated by use of alternative wavelengths are considered to be alternative representations of the XRD patterns of the crystalline material of the present disclosure and as such are within the scope of the present disclosure.

The PXRD patterns for each of Form 1, Form 2, Form 3, Form 4 and Form MH of EFdA shown in FIGS. 1, 4, 6, 7 and 10, respectively, were generated using the equipment and procedures described above. The intensity of the peaks (y-axis is in counts per second) for each PXRD pattern is plotted versus the 2 theta angle (x-axis is in degrees 2 theta). In addition, the data were plotted with detector counts normalized for the collection time per step versus the 2 theta angle. The XRD patterns in each of FIGS. 12, 13, 14 and 15 were generated as described for the PXRD patterns above, except that the samples used to obtain the XRD patterns were not bulk compositions but rather EFdA/EVA compositions in solid dosage form (long-acting polymeric parenteral implant).

Solid State $^{19}$F NMR (ssNMR): All solid-state $^{19}$F nuclear magnetic resonance (NMR)_spectra were acquired on a Bruker Avance III HD 9.4 T spectrometer equipped with a 4.0 mm H/F/X magic angle spinning (MAS) probe. The probe was tuned to F/H double resonance modes for $^{19}$F (fluorine-19) experiments. $^{19}$F direct polarization (DP) magic angle spinning (MAS) spectra were collected under 83.3 kHz $^{1}$H dipolar decoupling during acquisition and with a recycle delay of 60 s. Samples were spinning at a frequency of 12 kHz and maintained at 294 K for all experiments. Typical pulses were 4.0 us for $^{19}$F. $^{19}$F chemical shifts were referenced to the $^{19}$F signal of Teflon at −122.0 ppm.

The $^{19}$F NMR ssNMR spectrum for each of Form 1, Form 2, Form 4 and Form MH of EFdA, shown in FIGS. 2, 5, 8 and 11, respectively, were generated using the equipment and procedures described above.

Thermogravimetric Analysis (TGA): Thermal gravimetric analysis (TGA) data were acquired using a Perkin Elmer model TGA 7 or equivalent. Experiments were performed under a flow of nitrogen and using a heating rate of 10°

C./min to a maximum temperature of approximately 300° C. After automatically taring the balance, an appropriate amount of sample was added to the platinum pan, the furnace raised, and the heating program started. Analysis of the results were carried out by selecting the Delta Y function within the instrument software and choosing the temperatures between which the weight loss is to be calculated. Weight losses were reported up to the onset of decomposition/evaporation.

Using the thermogravimetric analysis equipment and procedure described above, Form 1 and Form 4 of EFdA were each separately subjected to TGA analysis.

Anhydrate Crystalline Form 1 of EFdA

Anhydrate Crystalline Form 1 of EFdA: X-Ray Diffraction (PXRD):

The PXRD pattern for Form 1 is displayed in FIG. 1. Thus, in an aspect of this disclosure, there is provided an anhydrate crystalline Form 1 of EFdA characterized by a powder x-ray diffraction pattern substantially as shown in FIG. 1. Peak locations (on the 2 theta x-axis) consistent with these profiles are displayed in Table 1 (+/−0.2° 2 theta). The locations of these PXRD peaks are characteristic of Form 1 of EFdA. Thus, in another aspect, anhydrate crystalline Form 1 of EFdA is characterized by a powder x-ray diffraction pattern having each of the peak positions listed in Table 1, +/−0.2° 2-theta.

TABLE 1

| Diagnostic Peak Set | Peak Location [°2Th.] (+/−0.2° 2-theta) | d-spacing [Å] | Relative intensity [%] | Peak No. |
|---|---|---|---|---|
| 1 | 4.48 | 19.73 | 68.9 | 1 |
| 2 | 8.99 | 9.84 | 48.6 | 2 |
|   | 10.16 | 8.71 | 15.9 | 3 |
| 3 | 10.39 | 8.51 | 46.0 | 4 |
| 1 | 11.79 | 7.50 | 54.2 | 5 |
| 2 | 12.39 | 7.14 | 36.5 | 6 |
| 1 | 14.70 | 6.03 | 41.2 | 7 |
| 3 | 15.51 | 5.71 | 36.3 | 8 |
|   | 15.98 | 5.55 | 17.1 | 9 |
|   | 16.64 | 5.33 | 20.1 | 10 |
| 2 | 16.88 | 5.25 | 58.2 | 11 |
|   | 17.39 | 5.10 | 13.6 | 12 |
| 3 | 18.09 | 4.91 | 60.3 | 13 |
|   | 18.30 | 4.85 | 16.3 | 14 |
| 3 | 20.16 | 4.40 | 67.1 | 15 |
|   | 21.69 | 4.10 | 13.4 | 16 |
|   | 24.96 | 3.57 | 43.7 | 17 |
| 1 | 25.81 | 3.45 | 100.0 | 18 |
| 2 | 27.42 | 3.25 | 92.7 | 19 |
|   | 29.69 | 3.01 | 13.0 | 20 |

Thus, in one aspect, anhydrate crystalline Form 1 of EFdA is characterized by a powder x-ray diffraction pattern having each of the peak locations listed in Table 1, +/−0.2° 2-theta.

In another aspect, anhydrate crystalline Form 1 of EFdA is characterized by a powder X-ray diffraction pattern comprising two or more of the 2-theta values listed in Table 1, +/−0.2° 2-theta.

In another aspect, anhydrate crystalline Form 1 of EFdA is characterized by a powder x-ray diffraction pattern comprising three or more of the 2-theta values listed in Table 1, +/−0.2° 2-theta.

In another aspect, anhydrate crystalline Form 1 of EFdA is characterized by a powder x-ray diffraction pattern comprising four or more of the 2-theta values listed in Table 1, +/−0.2° 2-theta.

In another aspect, anhydrate crystalline Form 1 of EFdA is characterized by a powder x-ray diffraction pattern comprising six or more of the 2-theta values listed in Table 1, +/−0.2° 2-theta.

In another aspect, anhydrate crystalline Form 1 of EFdA is characterized by a powder x-ray diffraction pattern comprising nine or more of the 2-theta values listed in Table 1, +/−0.2° 2-theta.

In another aspect, anhydrate crystalline Form 1 of EFdA is characterized by a powder x-ray diffraction pattern comprising twelve or more of the 2-theta values listed in Table 1, +/−0.2° 2-theta.

In a further aspect, the PXRD peak locations displayed in Table 1 and/or FIG. 1 most characteristic of anhydrate crystalline Form 1 of EFdA can be selected and grouped as "diagnostic peak sets" to conveniently distinguish this crystalline form from others. Selections of such characteristic peaks are set out in Table 1 in the column labeled Diagnostic Peak Set.

Thus, in another aspect, there is provided a crystalline Form anhydrate 1 of EFdA characterized by a powder x-ray diffraction pattern comprising each of the 2-theta values listed in Diagnostic Peak Set 1 in Table 1, +/−0.2° 2-theta.

In another aspect, there is provided an anhydrate crystalline Form 1 of EFdA characterized by a powder x-ray diffraction pattern comprising each of the 2-theta values listed in Diagnostic Peak Set 2 in Table 1, +/−0.2° 2-theta.

In another aspect, there is provided an anhydrate crystalline Form 1 of EFdA characterized by a powder x-ray diffraction pattern comprising each of the 2-theta values listed in Diagnostic Peak Set 3 in Table 1, +/−0.2° 2-theta.

In another aspect, there is provided an anhydrate crystalline Form 1 of EFdA characterized by a powder x-ray diffraction pattern comprising each of the 2-theta values listed in Diagnostic Peak Set 1 and Diagnostic Peak Set 2 in Table 1, +/−0.2° 2-theta.

In another aspect, there is provided an anhydrate crystalline Form 1 of EFdA characterized by a powder x-ray diffraction pattern comprising each of the 2-theta values listed in Diagnostic Peak Set 1 and Diagnostic Peak Set 3 in Table 1, +/−0.2° 2-theta.

In another aspect, there is provided an anhydrate crystalline Form 1 of EFdA characterized by a powder x-ray diffraction pattern comprising each of the 2-theta values listed in Diagnostic Peak Set 1 and Diagnostic Peak Set 2 and Diagnostic Peak Set 3 in Table 1, +/−0.2° 2-theta.

In another aspect, anhydrate crystalline Form 1 of EFdA is characterized by the PXRD spectrum as shown in FIG. 1.

In yet another aspect, anhydrate crystalline Form 1 of EFdA is characterized by the above described PXRD characteristic peaks and/or the data shown in FIG. 1, alone or in combination with any of the other characterizations of Form 1 of EFdA described herein.

Figure 2:
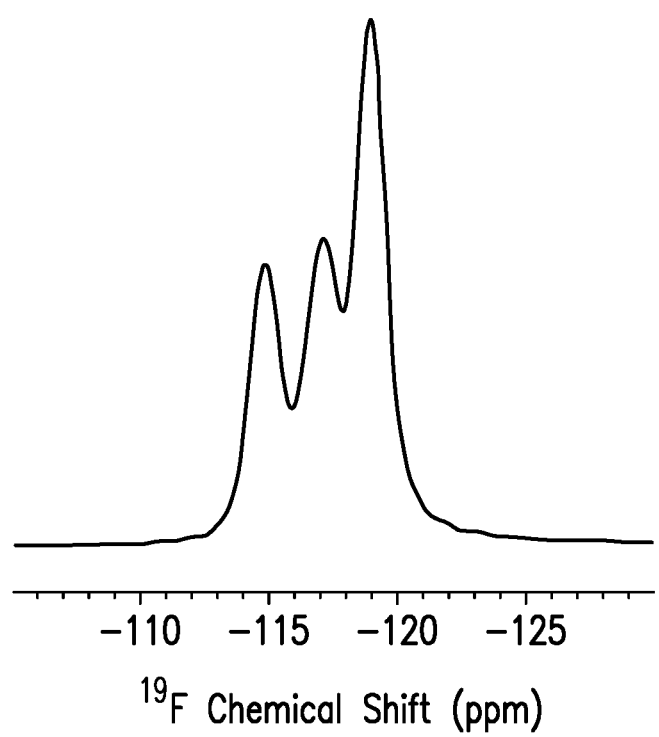
FIG. 2 depicts a solid state $^{19}F$ NMR (nuclear magnetic resonance) spectrum of anhydrate crystalline Form 1 of EFdA.

Anhydrate Crystalline Form 1 of EFdA: $^{19}$F (fluorine-19) solid state NMR:

Using the $^{19}$F (fluorine-19) solid state NMR equipment and procedures described above, the solid state $^{19}$F NMR spectrum for Form 1 of EFdA was obtained. The spectrum is shown in FIG. 2. Characteristic peaks for anhydrate crystalline Form 1 of EFdA are observed at −114.75, −117.09 and −118.92 ppm. This NMR measurement can be used, alone or in combination with any of the other characterizations of Form 1 described herein, to identify Form 1 of EFdA and to distinguish it from other crystal forms of EFdA.

Thus, in another aspect, anhydrate crystalline Form 1 of EFdA is characterized by a solid state $^{19}$F NMR spectrum having peaks at −114.75, −117.09 and −118.92 ppm.

In another aspect, anhydrate crystalline Form 1 of EFdA is characterized by a solid state $^{19}$F NMR spectrum comprising any two of the following peaks: −114.75, −117.09 and −118.92 ppm.

In another aspect, anhydrate crystalline Form 1 of EFdA is characterized by a solid state $^{19}$F NMR spectrum comprising at least the following peaks: −117.09 and −118.92 ppm.

In another aspect, anhydrate crystalline Form 1 of EFdA is characterized by a solid state $^{19}$F NMR spectrum as shown in FIG. 2.

In yet another aspect, Form 1 of EFdA is characterized by the above described NMR characteristic peaks and/or the data shown in FIG. 2, alone or in combination with any of the other characterizations of Form 1 of EFdA described herein.

Thus, in yet another aspect, Form 1 of EFdA is characterized by PXRD Peak Location Group 1, and/or by PXRD Peak Location Group 2, and/or by PXRD Peak Location Group 3, each as described above in Table 1 above, and each further characterized by:
1) a solid state $^{19}$F NMR spectrum having peaks at −114.75, −117.09 and −118.92 ppm; or
2) a solid state $^{19}$F NMR spectrum having any two of the following peaks:
   −114.75, −117.09 and −118.92 ppm; or
3) a solid state $^{19}$F NMR spectrum having peaks at:
   −117.09 and −118.92 ppm; or
4) a solid state $^{19}$F NMR spectrum substantially as shown in FIG. 2.

Figure 3:
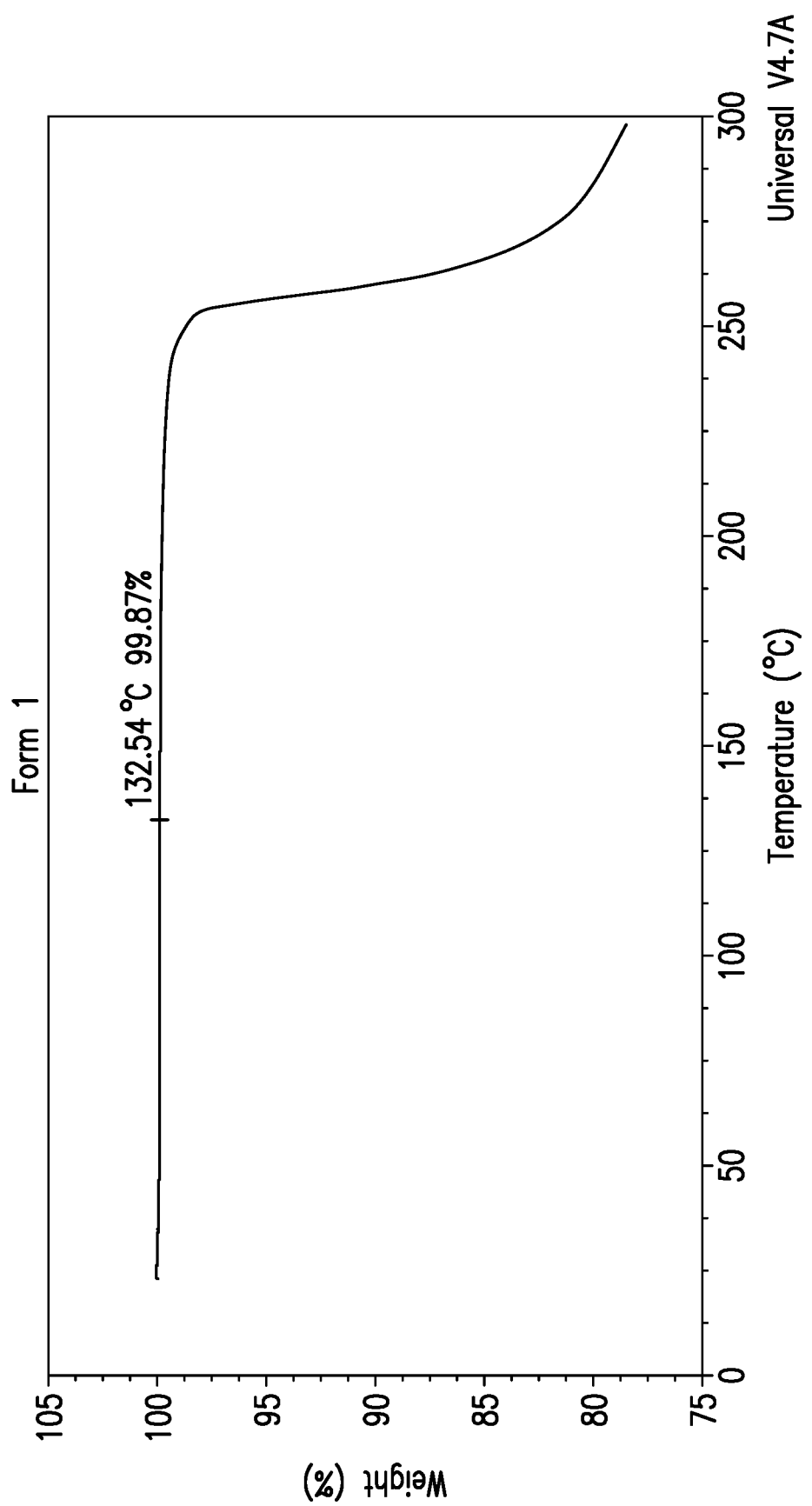
FIG. 3 is a graph of a thermal gravimetric analysis ("TGA") of anhydrate crystalline Form 1 of EFdA. The graph plots the weight (percentage) against temperature (° C.).

Anhydrate Crystalline Form 1 of EFdA: Thermogravimetric Analysis (TGA):

Using the thermogravimetric analysis equipment and procedures described above, Form 1 of EFdA was subjected to TGA analysis. FIG. 3 depicts a typical TGA analysis curve for Form 1 of EFdA. The data show 0.1 wt. % loss up to 133° C., followed by thermal decomposition above 240° C. This TGA analysis can be used, alone or in combination with any of the other characterizations of Form 1 described herein, to identify Form 1 of EFdA and to distinguish it from other crystal forms of EFdA. Thus, in another aspect, Form 1 of EFdA is characterized by a TGA curve substantially as shown in FIG. 3. In yet another aspect, Form 1 of EFdA is characterized by any of these TGA measurements and/or the TGA curve substantially as shown in FIG. 3, alone or in combination with any one or more of the other characterizations for Form 1 described herein, including each of the aspects of the PXRD characterizations described above, and/or each of the aspects of the $^{19}$F ssNMR characterizations described above for Form 1.

Anhydrate Crystalline Form 2 of EFdA

Anhydrate Crystalline Form 2 of EFdA: PXRD Pattern

Figure 4:
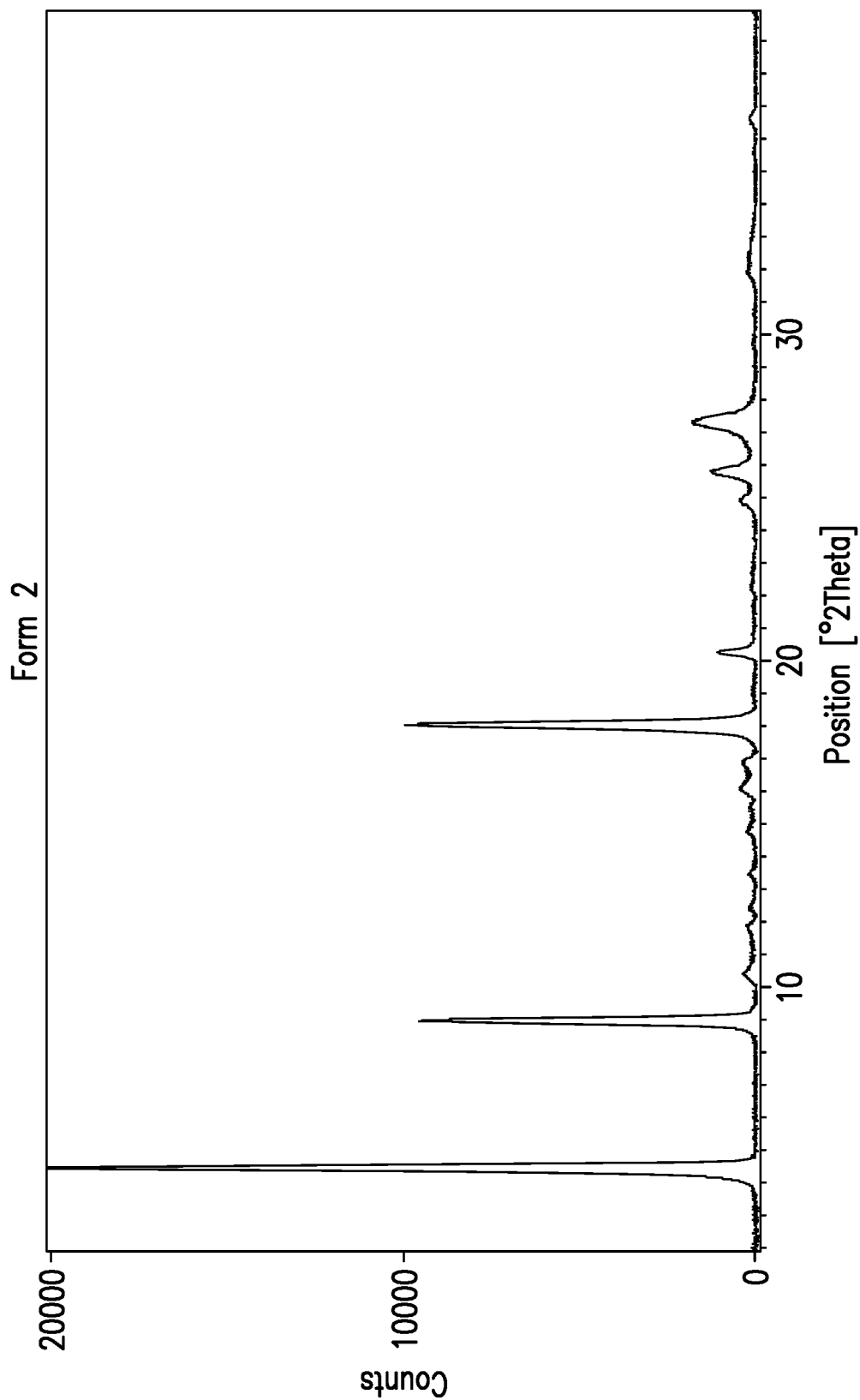
FIG. 4 is a graph of a Powder X-Ray Diffraction ("PXRD") pattern of anhydrate crystalline Form 2 of EFdA, generated using the equipment and methods described herein. The graph plots the intensity of the peaks as defined by counts per second versus the diffraction angle 2 theta (2Θ) in degrees.

The PXRD pattern for anhydrate crystalline Form 2 of EFdA is depicted in FIG. 4. Thus, in an aspect of this disclosure, there is provided an anhydrate crystalline Form 2 of EFdA characterized by a powder x-ray diffraction pattern substantially as shown in FIG. 4. Peak locations (on the 2 theta x-axis) consistent with these profiles are displayed in Table 2 (+/−0.2° 2 theta). The locations of these PXRD peaks are characteristic of anhydrate crystalline Form 2 of EFdA.

Thus, in another aspect, anhydrate crystalline Form 2 of EFdA is characterized by a powder x-ray diffraction pattern having each of the peak positions listed in Table 2, +/−0.2° 2-theta.

TABLE 2

| Peak Location [°2Th.] (+/−0.2° 2-theta) | d-spacing [Å] | Relative intensity [%] | Peak No. |
|---|---|---|---|
| 4.47 | 19.79 | 100.0 | 1 |
| 8.96 | 9.87 | 47.2 | 2 |
| 10.40 | 8.50 | 1.3 | 3 |
| 16.06 | 5.51 | 1.6 | 4 |
| 16.89 | 5.24 | 1.3 | 5 |
| 18.02 | 4.92 | 4.9 | 6 |
| 24.87 | 3.58 | 1.5 | 7 |
| 25.77 | 3.45 | 5.2 | 8 |
| 27.28 | 3.27 | 8.1 | 9 |

In another aspect, anhydrate crystalline Form 2 of EFdA is characterized by a powder X-ray diffraction pattern comprising two or more of the 2-theta values listed in Table 2, +/−0.2° 2-theta.

In another aspect, anhydrate crystalline Form 2 of EFdA is characterized by a powder x-ray diffraction pattern comprising three or more of the 2-theta values listed in Table 2, +/−0.2° 2-theta.

In another aspect, anhydrate crystalline Form 2 of EFdA is characterized by a powder x-ray diffraction pattern comprising four or more of the 2-theta values listed in Table 2, +/−0.2° 2-theta.

In another aspect, anhydrate crystalline Form 2 of EFdA is characterized by a powder x-ray diffraction pattern comprising six or more of the 2-theta values listed in Table 2, +/−0.2° 2-theta.

Anhydrate Crystalline Form 2 of EFdA: $^{19}$F (fluorine-19) Solid State NMR

Figure 5:
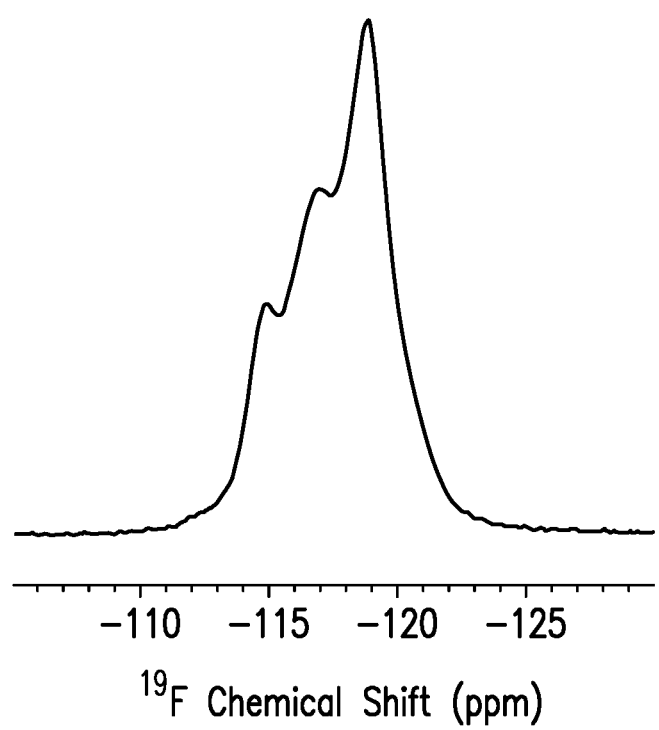
FIG. 5 depicts a solid state $^{19}F$ NMR (nuclear magnetic resonance) spectrum of anhydrate crystalline Form 2 of EFdA.

Using the $^{19}$F (fluorine-19) solid state NMR equipment and procedures described above, the solid state $^{19}$F NMR spectrum for anhydrate crystalline Form 2 of EFdA was obtained. The $^{19}$F NMR spectrum for anhydrate crystalline Form 2 is shown in FIG. 5. Characteristic peaks for anhydrate crystalline Form 2 of EFdA are observed at −114.73, −116.74 and −118.78 ppm. This NMR measurement can be used, alone or in combination with any of the other characterizations of Form 2 described herein, to identify Form 2 of EFdA and to distinguish it from other crystal forms of EFdA.

Thus, in another aspect, anhydrate crystalline Form 2 of EFdA is characterized by a solid state $^{19}$F NMR spectrum having peaks at −114.73, −116.74 and −118.78 ppm.

In another aspect, anhydrate crystalline Form 2 of EFdA is characterized by a solid state $^{19}$F NMR spectrum comprising any two of the following peaks: −114.73, −116.74 and −118.78 ppm. In another aspect, anhydrate crystalline Form 2 of EFdA is characterized by a solid state $^{19}$F NMR spectrum comprising the following peaks: −116.74 and −118.78 ppm.

In another aspect, Form 2 of EFdA is characterized by a solid state $^{19}$F NMR spectrum as shown in FIG. 5.

In another aspect, anhydrate crystalline Form 2 of EFdA is characterized by solid state $^{19}$F NMR spectrum having peaks at −114.73, −116.74 and −118.78 ppm in combination with any one or more PXRD Peaks in Table 2 or aspects thereof as described above.

In another aspect, anhydrate crystalline Form 2 of EFdA is characterized by a solid state $^{19}$F NMR data as shown in FIG. 5 in combination with any one or more of PXRD Peaks in Table 2 or aspects thereof as described above.

Anhydrate Crystalline Form 3 of EFdA

Anhydrate Crystalline Form 3 of EFdA: PXRD Pattern

Figure 6:
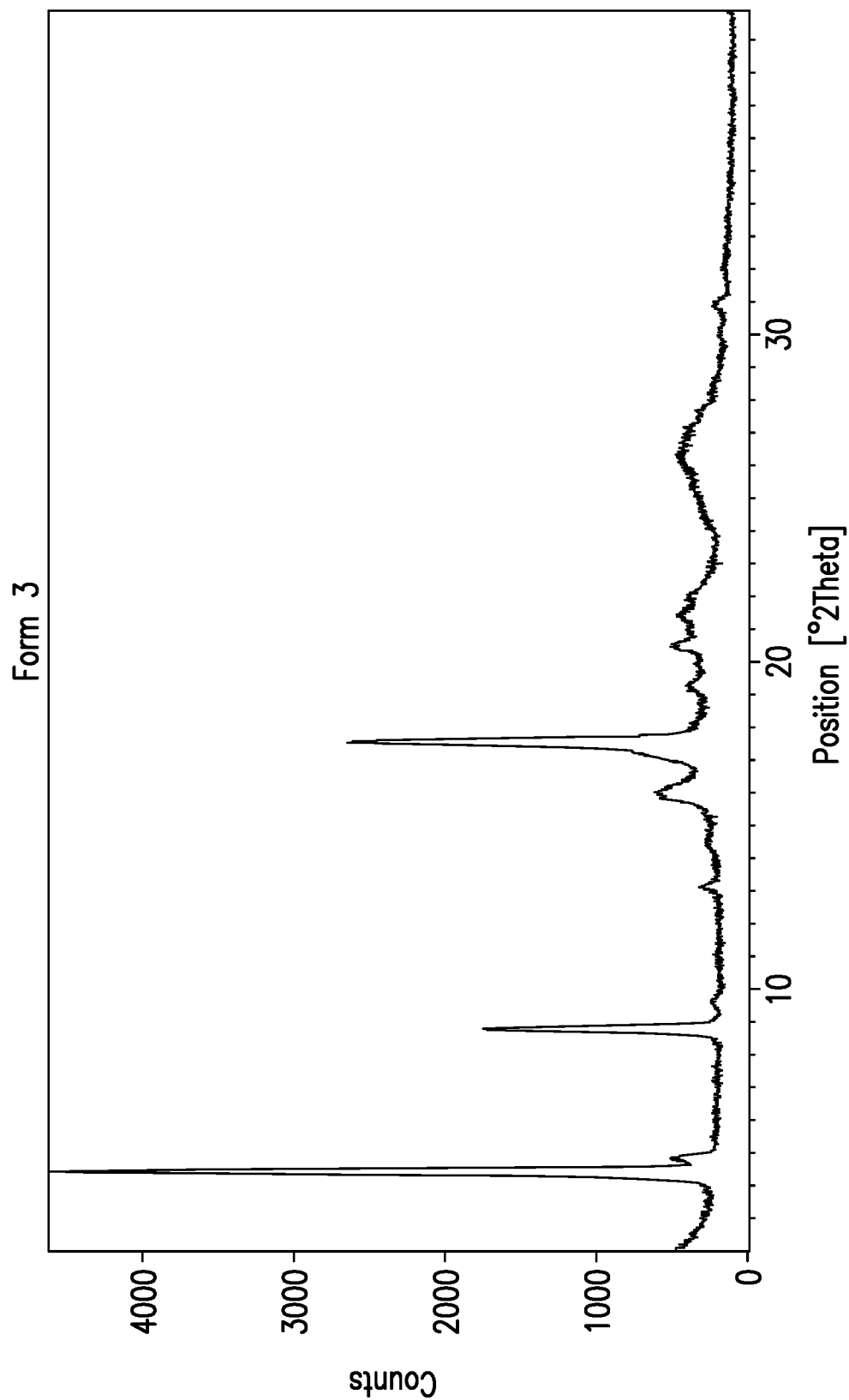
FIG. 6 is a graph of a Powder X-Ray Diffraction ("PXRD") pattern of anhydrate crystalline Form 3 of EFdA, generated using the equipment and methods described herein. The graph plots the intensity of the peaks as defined by counts per second versus the diffraction angle 2 theta (2Θ) in degrees.

The PXRD pattern for anhydrate crystalline Form 3 of EFdA is depicted in FIG. 6. Thus, in an aspect of this disclosure, there is provided an anhydrate crystalline Form 3 of EFdA characterized by a powder x-ray diffraction pattern substantially as shown in FIG. 6. Peak locations (on the 2 theta x-axis) consistent with these profiles are displayed in Table 3 (+/−0.2° 2 theta). The locations of these PXRD peaks are characteristic of anhydrate crystalline Form 3 of EFdA.

Thus, in another aspect, anhydrate crystalline Form 3 of EFdA is characterized by a powder x-ray diffraction pattern having each of the peak positions listed in Table 3, +/−0.2° 2-theta.

TABLE 3

| Peak Location [°2Th.] (+/−0.2° 2-theta) | d-spacing [Å] | Relative intensity [%] | Peak No. |
|---|---|---|---|
| 4.33 | 20.42 | 100.0 | 1 |
| 8.69 | 10.18 | 33.9 | 2 |
| 9.52 | 9.28 | 1.0 | 3 |
| 13.05 | 6.78 | 2.6 | 4 |
| 15.77 | 5.62 | 5.6 | 5 |
| 16.98 | 5.22 | 4.6 | 6 |
| 17.47 | 5.08 | 51.3 | 7 |
| 19.21 | 4.62 | 1.8 | 8 |
| 20.37 | 4.36 | 3.1 | 9 |
| 21.35 | 4.20 | 1.1 | 10 |
| 26.90 | 3.31 | 1.3 | 11 |

In another aspect, anhydrate crystalline Form 3 of EFdA is characterized by a powder X-ray diffraction pattern comprising two or more of the 2-theta values listed in Table 3, +/−0.2° 2-theta.

In another aspect, anhydrate crystalline Form 3 of EFdA is characterized by a powder x-ray diffraction pattern comprising three or more of the 2-theta values listed in Table 3, +/−0.2° 2-theta.

In another aspect, anhydrate crystalline Form 3 of EFdA is characterized by a powder x-ray diffraction pattern comprising four or more of the 2-theta values listed in Table 3, +/−0.2° 2-theta.

In another aspect, anhydrate crystalline Form 3 of EFdA is characterized by a powder x-ray diffraction pattern comprising six or more of the 2-theta values listed in Table 3, +/−0.2° 2-theta.

Anhydrate Crystalline Form 4 of EFdA

Anhydrate Crystalline Form 4 of EFdA: Powder X-Ray Diffraction (PXRD)

Figure 7:
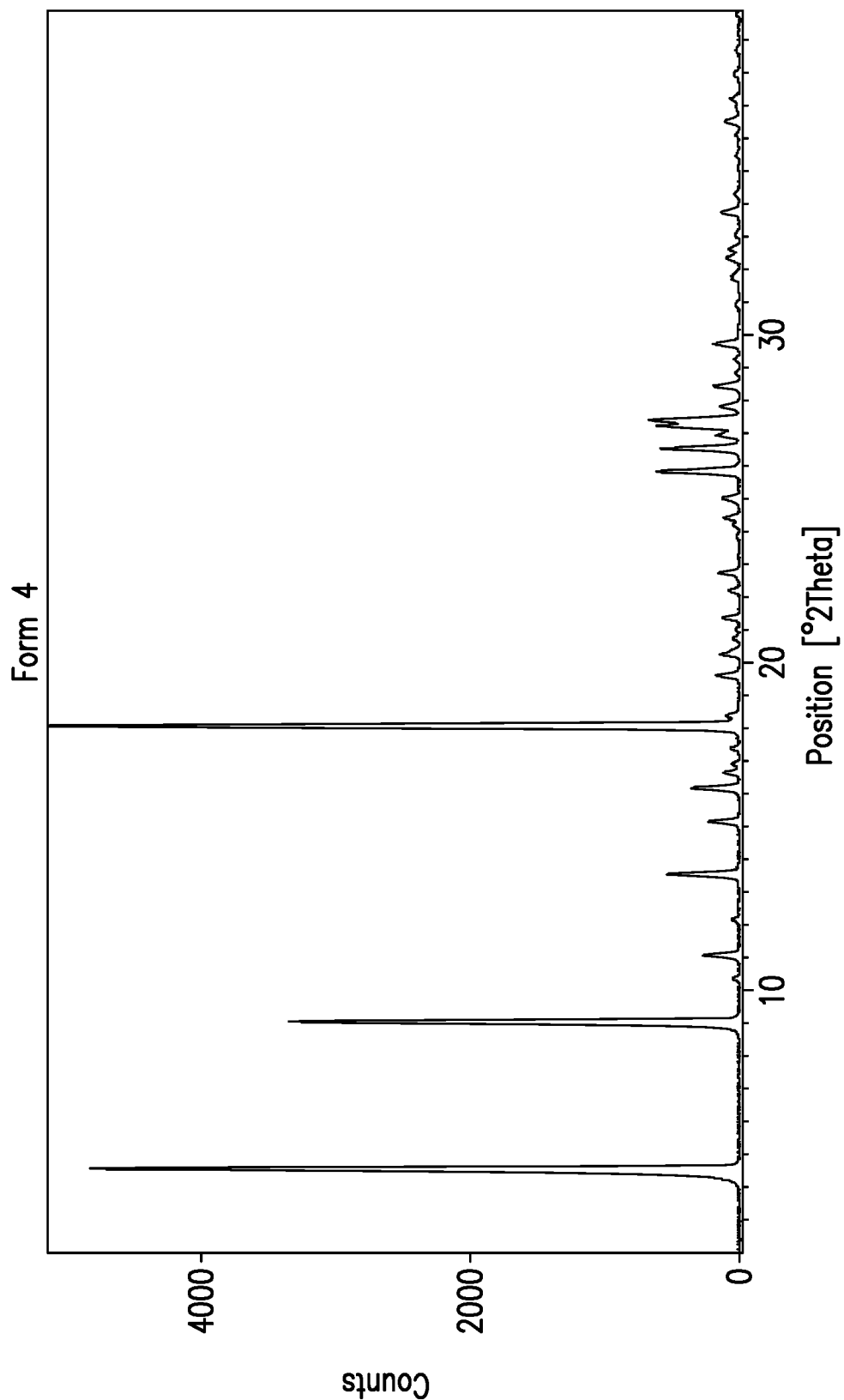
FIG. 7 is a graph of a Powder X-Ray Diffraction ("PXRD") pattern of anhydrate crystalline Form 4 of EFdA, generated using the equipment and methods described herein. The graph plots the intensity of the peaks as defined by counts per second versus the diffraction angle 2 theta (2Θ) in degrees.

The PXRD pattern for anhydrate crystalline Form 4 of EFdA is displayed in FIG. 7. Thus, in an aspect of this disclosure, there is provided an anhydrate crystalline Form 4 of EFdA characterized by a powder x-ray diffraction pattern substantially as shown in FIG. 7. Peak locations (on the 2 theta x-axis) consistent with these profiles are displayed in Table 4 (+/−0.2° 2 theta). The locations of these PXRD peaks are characteristic of anhydrate crystalline Form 4 of EFdA. Thus, in another aspect, anhydrate crystalline Form 4 of EFdA is characterized by a powder x-ray diffraction pattern having each of the peak positions listed in Table 4, +/−0.2° 2-theta.

TABLE 4

| Diagnostic Peak Set | Peak Location [°2Th.] (+/−0.2° 2-theta) | d-spacing [Å] | Relative intensity [%] | Peak No. |
|---|---|---|---|---|
| 2 | 4.48 | 19.73 | 68.9 | 1 |
| 3 | 8.99 | 9.87 | 48.6 | 2 |
| 4 | 10.16 | 8.71 | 15.9 | 3 |
| 3 | 10.39 | 8.51 | 46.0 | 4 |
| 1 | 11.79 | 7.50 | 54.2 | 5 |
| 1 | 12.39 | 7.14 | 36.5 | 6 |
| 1 | 14.70 | 6.03 | 41.2 | 7 |
| 1 | 15.51 | 5.71 | 36.3 | 8 |
| 4 | 15.98 | 5.55 | 17.1 | 9 |
| 4 | 16.64 | 5.33 | 20.1 | 10 |
| 3 | 16.88 | 5.25 | 59.2 | 11 |
|  | 17.39 | 5.10 | 13.6 | 12 |
| 2 | 18.09 | 4.91 | 60.3 | 13 |
|  | 18.30 | 4.85 | 16.3 | 14 |
| 3 | 20.16 | 4.40 | 67.1 | 15 |
|  | 21.69 | 4.10 | 13.4 | 16 |
| 4 | 24.96 | 3.57 | 43.7 | 17 |
| 2 | 25.81 | 3.45 | 100.0 | 18 |
| 2 | 27.42 | 3.25 | 92.7 | 19 |
|  | 29.69 | 3.01 | 13.0 | 20 |

Thus, in one aspect, anhydrate crystalline Form 4 of EFdA is characterized by a powder x-ray diffraction pattern having each of the peak locations listed in Table 4, +/−0.2° 2-theta.

In another aspect, anhydrate crystalline Form 4 of EFdA is characterized by a powder x-ray diffraction pattern comprising two or more of the 2-theta values listed in Table 4, +/−0.2° 2-theta.

In another aspect, anhydrate crystalline Form 4 of EFdA is characterized by a powder x-ray diffraction pattern comprising three or more of the 2-theta values listed in Table 4, +/−0.2° 2-theta.

In another aspect, anhydrate crystalline Form 4 of EFdA is characterized by a powder x-ray diffraction pattern comprising four or more of the 2-theta values listed in Table 4, +/−0.2° 2-theta.

In another aspect, anhydrate crystalline Form 4 of EFdA is characterized by a powder x-ray diffraction pattern comprising six or more of the 2-theta values listed in Table 4, +/−0.2° 2-theta.

In another aspect, anhydrate crystalline Form 4 of EFdA is characterized by a powder x-ray diffraction pattern comprising nine or more of the 2-theta values listed in Table 4, +/−0.2° 2-theta.

In another aspect, anhydrate crystalline Form 4 of EFdA is characterized by a powder x-ray diffraction pattern comprising twelve or more of the 2-theta values listed in Table 4, +/−0.2° 2-theta.

In a further aspect, the PXRD peak locations displayed in Table 4 and/or FIG. 7 most characteristic of anhydrate crystalline Form 4 of EFdA can be selected and grouped as "diagnostic peak sets" to conveniently distinguish this crystalline form from others. Selections of such characteristic peaks are set out in Table 4 in the column labeled Diagnostic Peak Set.

Thus, in another aspect, there is provided an anhydrate crystalline Form 4 of EFdA characterized by a powder x-ray diffraction pattern comprising each of the 2-theta values listed in Diagnostic Peak Set 1 in Table 4, +/−0.2° 2-theta.

In another aspect, there is provided an anhydrate crystalline Form 4 of EFdA characterized by a powder x-ray diffraction pattern comprising each of the 2-theta values listed in Diagnostic Peak Set 2 in Table 4, +/−0.2° 2-theta.

In another aspect, there is provided an anhydrate crystalline Form 4 of EFdA characterized by a powder x-ray diffraction pattern comprising each of the 2-theta values listed in Diagnostic Peak Set 3 in Table 4, +/−0.2° 2-theta.

In another aspect, there is provided an anhydrate crystalline Form 4 of EFdA characterized by a powder x-ray diffraction pattern comprising each of the 2-theta values listed in Diagnostic Peak Set 4 in Table 4, +/−0.2° 2-theta.

In another aspect, there is provided an anhydrate crystalline Form 4 of EFdA characterized by a powder x-ray diffraction pattern comprising each of the 2-theta values listed in Diagnostic Peak Set 1 and any one or more of Diagnostic Peak Set 2, Diagnostic Peak Set 3, and/or Diagnostic Peak Set 4 in Table 4, +/−0.2° 2-theta.

In another aspect, there is provided an anhydrate crystalline Form 4 of EFdA characterized by a powder x-ray diffraction pattern comprising each of the 2-theta values listed in Diagnostic Peak Set 2 and any one or more of Diagnostic Peak Set 1, Diagnostic Peak Set 3, and/or Diagnostic Peak Set 4 in Table 4, +/−0.2° 2-theta.

In another aspect, there is provided an anhydrate crystalline Form 4 of EFdA characterized by a powder x-ray diffraction pattern comprising each of the 2-theta values listed in Diagnostic Peak Set 3 and any one or more of Diagnostic Peak Set 1, Diagnostic Peak Set 2, and/or Diagnostic Peak Set 4 in Table 4, +/−0.2° 2-theta.

In another aspect, there is provided an anhydrate crystalline Form 4 of EFdA characterized by a powder x-ray diffraction pattern comprising each of the 2-theta values listed in Diagnostic Peak Set 4 and any one or more of Diagnostic Peak Set 1, Diagnostic Peak Set 2, and/or Diagnostic Peak Set 3 in Table 4, +/−0.2° 2-theta.

In another aspect, anhydrate crystalline Form 4 of EFdA is characterized by the PXRD spectrum as shown in FIG. 7.

In yet another aspect, anhydrate crystalline Form 4 of EFdA is characterized by the above described PXRD characteristic peaks and/or the data shown in FIG. 7, alone or in combination with any of the other characterizations of Form 4 of EFdA described herein.

Figure 8:
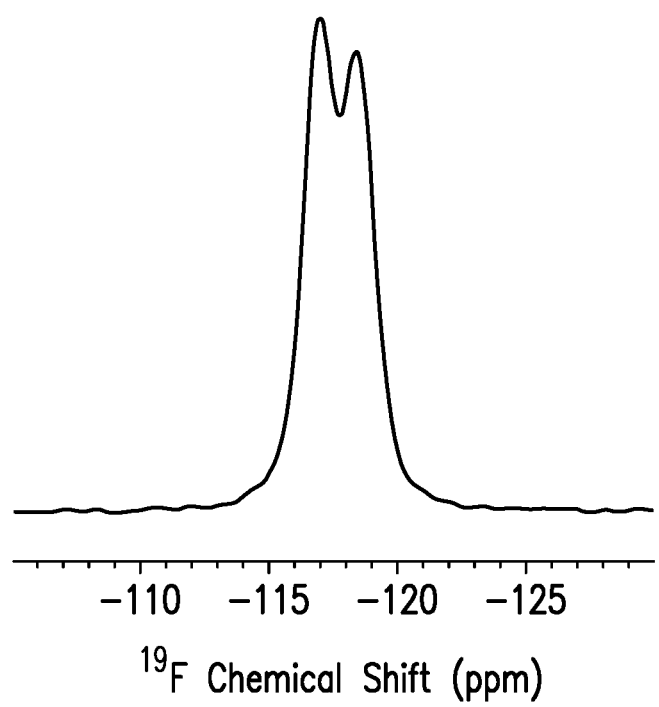
FIG. 8 depicts a solid state $^{19}F$ NMR (nuclear magnetic resonance) spectrum of anhydrate crystalline Form 4 of EFdA.

Anhydrate Crystalline Form 4 of EFdA: $^{19}F$ (fluorine-19) solid state NMR:

Using the $^{19}F$ (fluorine-19) solid state NMR equipment and procedures described above, the solid state $^{19}F$ NMR spectrum for Form 4 of EFdA was obtained. The spectrum is shown in FIG. 8. Characteristic peaks for Form 4 of EFdA are observed at −114.75, −117.09 and −118.92 ppm. This NMR measurement can be used, alone or in combination with any of the other characterizations of Form 4 described herein, to identify Form 4 of EFdA and to distinguish it from other crystal forms of EFdA.

Thus, in another aspect, Form 4 of EFdA is characterized by a solid state $^{19}F$ NMR spectrum having at least any two of the following peaks 114.75, −117.09 and −118.92 ppm. In another aspect, Form 4 of EFdA is characterized by a solid state $^{19}F$ NMR spectrum comprising at least the following peaks: −116.96 and −118.36 ppm.

In another aspect, Form 4 of EFdA is characterized by a solid state $^{19}F$ NMR spectrum as shown in FIG. 8.

Thus in yet another aspect, Form 4 of EFdA is characterized by the above described NMR characteristic peaks and/or the data shown in FIG. 8, alone or in combination with any of the other characterizations of Form 4 of EFdA described herein.

Thus, in yet another aspect, Form 4 of EFdA is characterized by PXRD Peak Location Group 1, and/or by PXRD Peak Location Group 2, and/or by PXRD Peak Location Group 3, and/or by PXRD Peak Location Group 4, each as described above in Table 4, and each further characterized by:

1) a solid state $^{19}F$ NMR spectrum having peaks at −114.75, −117.09 and −118.92 ppm; or
2) a solid state $^{19}F$ NMR spectrum having at least two of the following peaks −114.75, −117.09 and −118.92 ppm; or
3) a solid state $^{19}F$ NMR spectrum having the following peaks: −116.96 and −118.36 ppm; or
4) a solid state $^{19}F$ NMR spectrum substantially as shown in FIG. 8.

Figure 9:
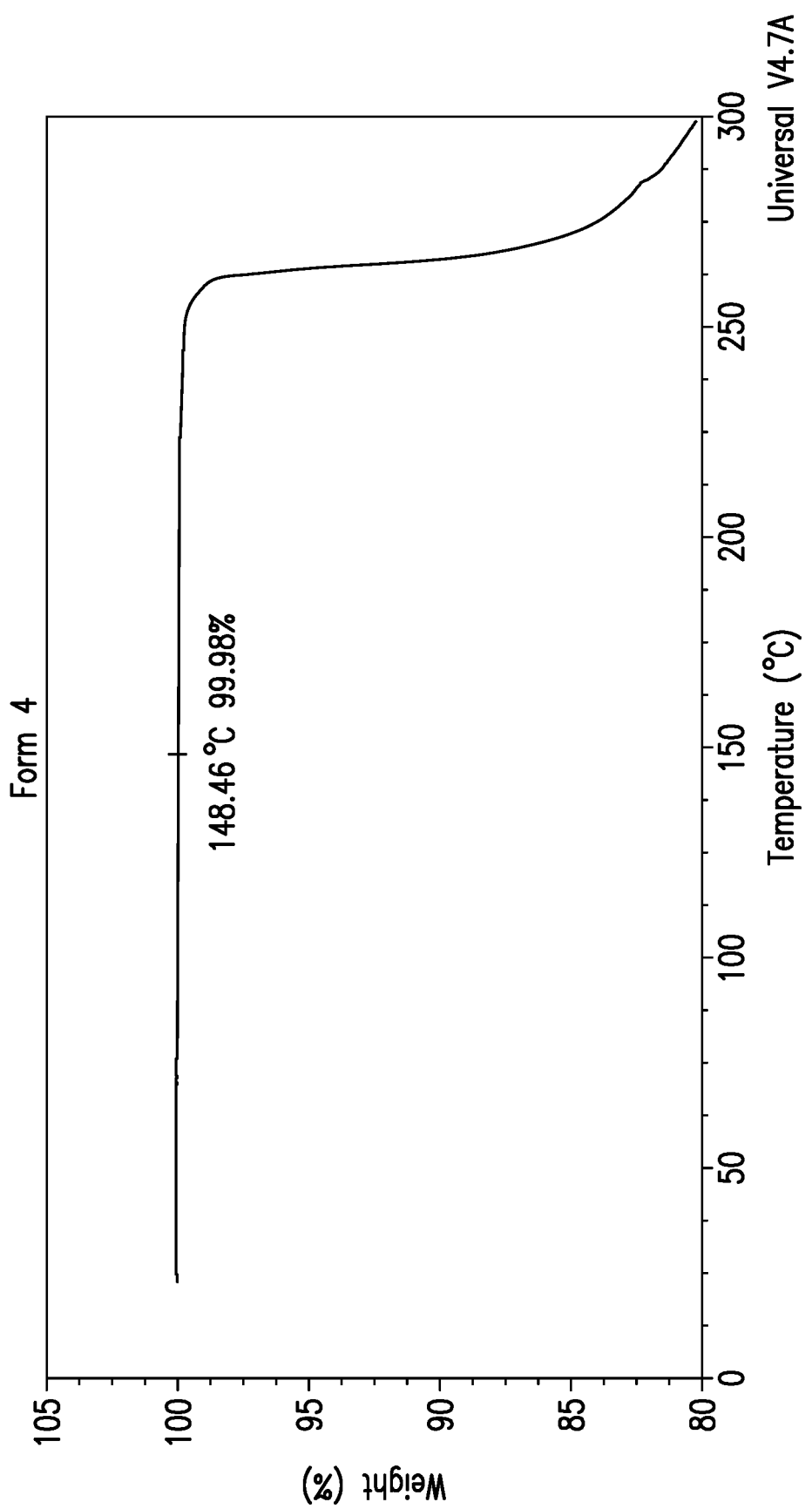
FIG. 9 is a graph of a thermal gravimetric analysis ("TGA") of anhydrate crystalline Form 4 of EFdA. The graph plots the weight (percentage) against temperature (° C.).

Anhydrate Crystalline Form 4 of EFdA: Thermogravimetric Analysis (TGA):

Using the thermogravimetric analysis equipment and procedures described above, Form 4 of EFdA was subjected to TGA analysis. FIG. 9 depicts a typical TGA analysis curve for Form 4 of EFdA. The data show 0.02 wt. % loss up to 148° C., followed by thermal decomposition above 250° C. This TGA analysis can be used, alone or in combination with any of the other characterizations of Form 4 described herein, to identify Form 4 of EFdA and to distinguish it from other crystal forms of EFdA. Thus, in another aspect, Form 4 of EFdA is characterized by a TGA curve substantially as shown in FIG. 9. In yet another aspect, Form 4 of EFdA is characterized by any of these TGA measurements and/or the TGA curve substantially as shown in FIG. 9, alone or in combination with any one or more of the other characterizations described herein, including each of the aspects of PXRD characterizations described above, and/or each of the aspects of $^{19}F$ ssNMR described above for Form 4.

Monohydrate Crystalline Form MH: PXRD Pattern

Figure 10:
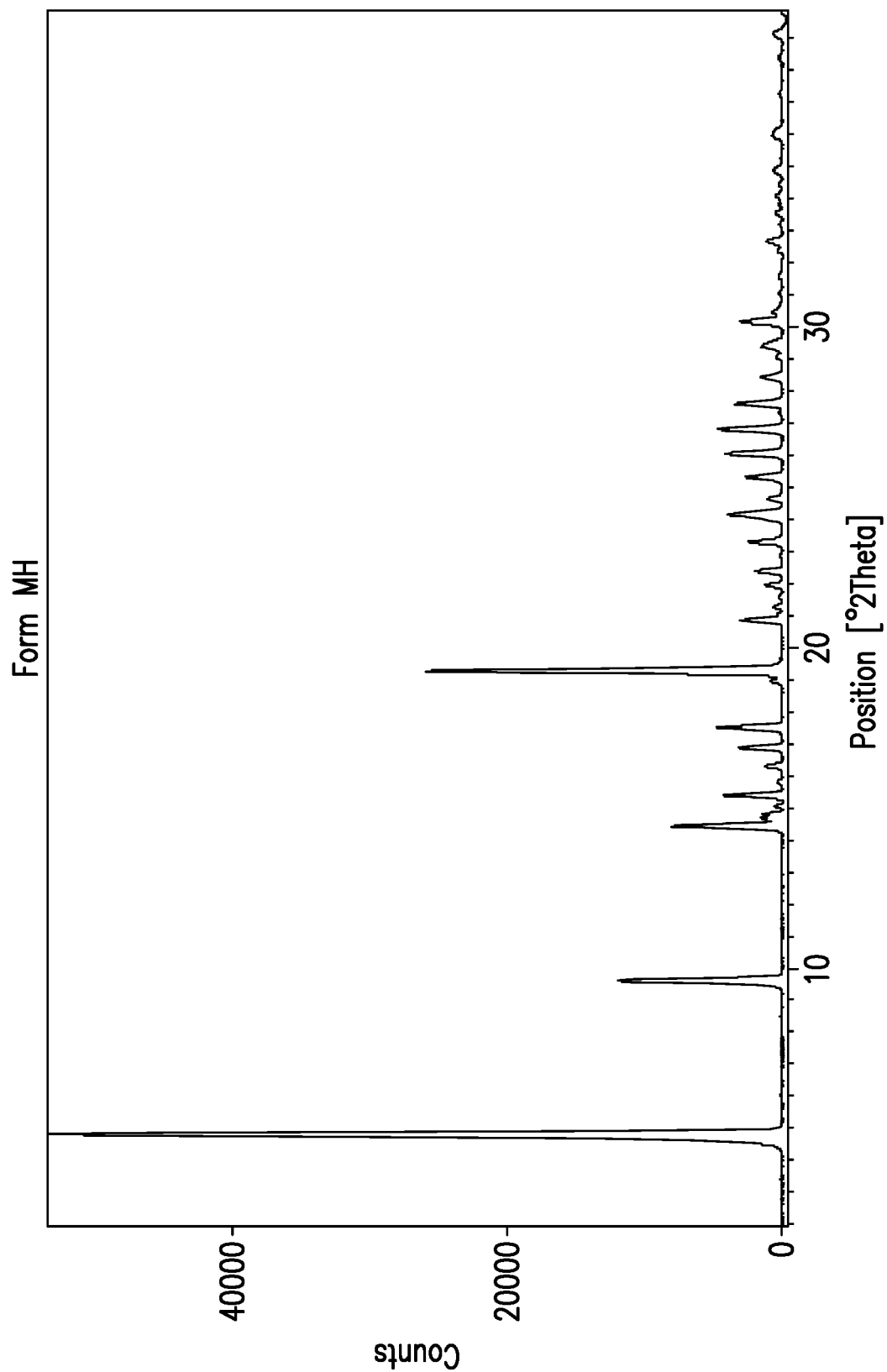
FIG. 10 is a graph of a Powder X-Ray Diffraction ("PXRD") pattern of monohydrate crystalline Form MH of EFdA, generated using the equipment and methods described herein. The graph plots the intensity of the peaks as defined by counts per second versus the diffraction angle 2 theta (2Θ) in degrees.

The PXRD pattern for Form MH is displayed in FIG. 10. Thus, in an aspect of this disclosure, there is provided a monohydrate crystalline Form MH of EFdA characterized by a powder x-ray diffraction pattern substantially as shown in FIG. 10. Peak locations (on the 2 theta x-axis) consistent with these profiles are displayed in Table 5 (+/−0.2° 2 theta). The locations of these PXRD peaks are characteristic of Form MH of EFdA. Thus, in another aspect, anhydrate crystalline Form MH of EFdA is characterized by a powder x-ray diffraction pattern having each of the peak positions listed in Table 5, +/−0.2° 2-theta.

TABLE 5

| Peak Location [°2Th.] (+/−0.2° 2-theta) | d-spacing [Å] | Relative intensity [%] | Peak No. |
| --- | --- | --- | --- |
| 4.78 | 18.47 | 100.0 | 1 |
| 9.58 | 9.24 | 22.2 | 2 |
| 14.40 | 6.15 | 14.9 | 3 |
| 15.35 | 5.77 | 7.9 | 4 |
| 16.27 | 5.44 | 2.2 | 5 |
| 16.85 | 5.26 | 5.9 | 6 |
| 17.48 | 5.07 | 8.9 | 7 |
| 19.25 | 4.61 | 48.4 | 8 |
| 20.83 | 4.27 | 5.6 | 9 |
| 24.13 | 3.69 | 7.3 | 10 |
| 25.29 | 3.52 | 5.0 | 11 |
| 26.03 | 3.42 | 7.8 | 12 |
| 26.79 | 3.33 | 8.6 | 13 |
| 27.58 | 3.23 | 6.3 | 14 |
| 30.14 | 2.96 | 5.7 | 15 |

Thus, in one aspect, monohydrate crystalline Form MH of EFdA is characterized by a powder x-ray diffraction pattern having each of the peak locations listed in Table 5, +/−0.2° 2-theta.

In another aspect, monohydrate crystalline Form MH of EFdA is characterized by a powder X-ray diffraction pattern comprising two or more of the 2-theta values listed in Table 5, +/−0.2° 2-theta.

In another aspect, monohydrate crystalline Form MH of EFdA is characterized by a powder x-ray diffraction pattern comprising three or more of the 2-theta values listed in Table 5, +/−0.2° 2-theta.

In another aspect, monohydrate crystalline Form MH of EFdA is characterized by a powder x-ray diffraction pattern comprising four or more of the 2-theta values listed in Table 5, +/−0.2° 2-theta.

In another aspect, monohydrate crystalline Form MH of EFdA is characterized by a powder x-ray diffraction pattern comprising six or more of the 2-theta values listed in Table 5, +/−0.2° 2-theta.

In another aspect, monohydrate crystalline Form MH of EFdA is characterized by a powder x-ray diffraction pattern comprising nine or more of the 2-theta values listed in Table 5, +/−0.2° 2-theta.

In another aspect, monohydrate crystalline Form MH of EFdA is characterized by a powder x-ray diffraction pattern comprising twelve or more of the 2-theta values listed in Table 5, +/−0.2° 2-theta.

In a further aspect, the PXRD peak locations displayed in Table 5 and/or FIG. 10 most characteristic of monohydrate crystalline Form MH of EFdA can be selected and grouped as "diagnostic peak sets" to conveniently distinguish this crystalline form from others. Selections of such characteristic peaks are set out in Table 5 in the column labeled Diagnostic Peak Set.

Thus, in another aspect, there is provided a monohydrate crystalline Form MH of EFdA characterized by a powder x-ray diffraction pattern comprising each of the 2-theta values listed in Diagnostic Peak Set 1 in Table 5, +/−0.2° 2-theta.

In another aspect, there is provided a monohydrate crystalline Form MH of EFdA characterized by a powder x-ray diffraction pattern comprising each of the 2-theta values listed in Diagnostic Peak Set 2 in Table 5, +/−0.2° 2-theta.

In another aspect, there is provided a monohydrate crystalline Form MH of EFdA characterized by a powder x-ray diffraction pattern comprising each of the 2-theta values listed in Diagnostic Peak Set 3 in Table 5, +/−0.2° 2-theta.

In another aspect, there is provided a monohydrate crystalline Form MH of EFdA characterized by a powder x-ray diffraction pattern comprising each of the 2-theta values listed in Diagnostic Peak Set 1 and Diagnostic Peak Set 2 in Table 5, +/−0.2° 2-theta.

In another aspect, there is provided a monohydrate crystalline Form MH of EFdA characterized by a powder x-ray diffraction pattern comprising each of the 2-theta values listed in Diagnostic Peak Set 1 and Diagnostic Peak Set 3 in Table 5, +/−0.2° 2-theta.

In another aspect, there is provided a monohydrate crystalline Form MH of EFdA characterized by a powder x-ray diffraction pattern comprising each of the 2-theta values listed in Diagnostic Peak Set 1 and Diagnostic Peak Set 2 and Diagnostic Peak Set 3 in Table 5, +/−0.2° 2-theta.

Figure 11:
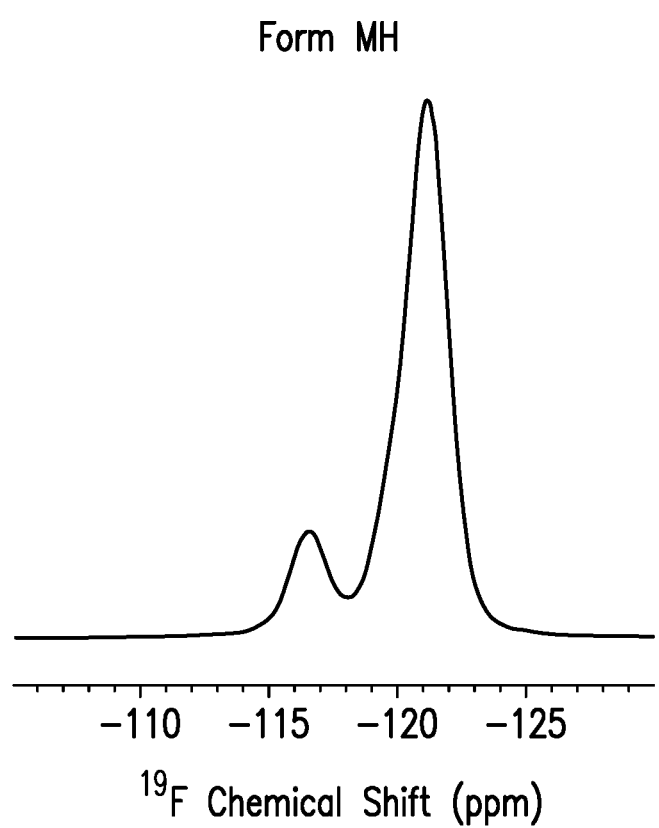
FIG. 11 depicts a solid state $^{19}F$ NMR (nuclear magnetic resonance) spectrum of monohydrate crystalline Form MH of EFdA.

Form MH $^{19}F$ (fluorine-19) Solid State NMR:

Using the $^{19}F$ (fluorine-19) solid state NMR equipment and procedures described above, the solid state $^{19}F$ NMR spectrum for monohydrate Form MH of EFdA was obtained. The $^{19}F$ NMR spectrum for monohydrate Form MH is shown in FIG. 11. Characteristic peaks for Form MH are observed at −116.52 and −121.13 ppm. This NMR measurement can be used, alone or in combination with the PXRD characterization data described in Table 5, to identify Form MH of EFdA and to distinguish it from other crystal forms of EFdA.

In another aspect, Form MH of EFdA is characterized by a solid state $^{19}F$ NMR spectrum having peaks −116.52 and/or −121.13 ppm.

Thus, in another aspect, monohydrate Form MH of EFdA is characterized by a solid state $^{19}F$ NMR spectrum as shown in FIG. 11.

In another aspect, Form MH of EFdA is characterized by the above described NMR characteristic peaks in combination with any one or more PXRD Peaks in Table 5 or aspects thereof as described above.

When utilizing the monohydrate Form MH, in-situ recrystallization occurs during said formulation processing, which results in conversion into a mixture of multiple, thermodynamically disfavored anhydrate phases in the drug product. In contrast, utilizing the thermodynamically stable Form 4 to manufacture the drug product results in the same thermodynamically stable "Form 4" being maintained throughout the processing and into the drug product. Therefore, unlike Form MH, Form 4 can be utilized to prevent phase conversions of EFdA into thermodynamically disfavored API phases during HME formulation processing of the implant drug product.

Similarly, "Form 1" is also physically stable in the implant HME manufacturing process, being maintained throughout the processing and into the drug product, unlike the monohydrate Form MH.

Figure 12:
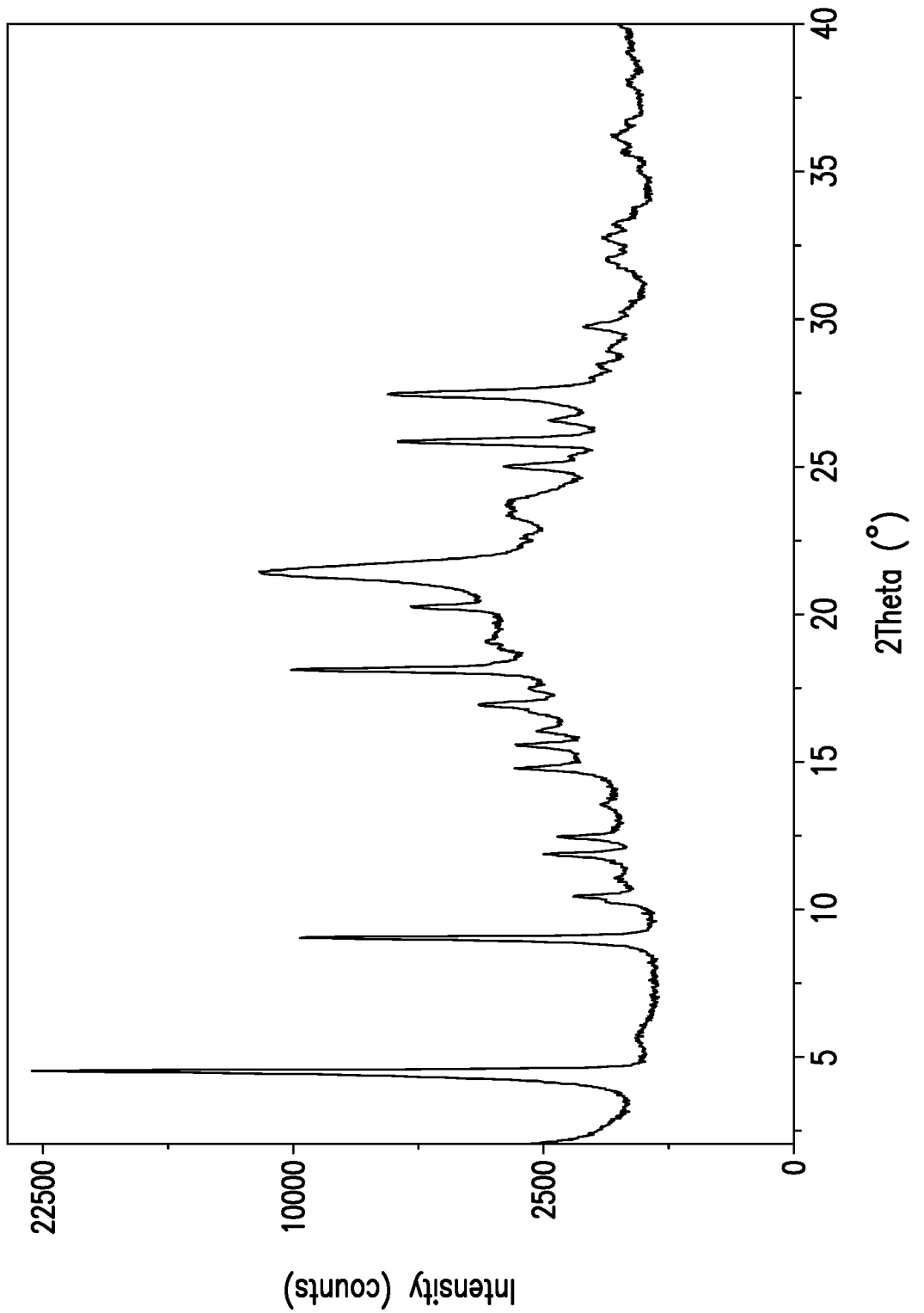
FIG. 12 is a graph of an X-Ray Diffraction ("XRD") pattern of a composition of monohydrate crystalline Form MH of EFdA and EVA polymer after undergoing hot melt extrusion processing with HME low shear Process A which resulted in conversion of Form MH to anhydrate crystalline Form 1 of EFdA and anhydrate crystalline Form 2 of EFdA in the composition.
Figure 13:
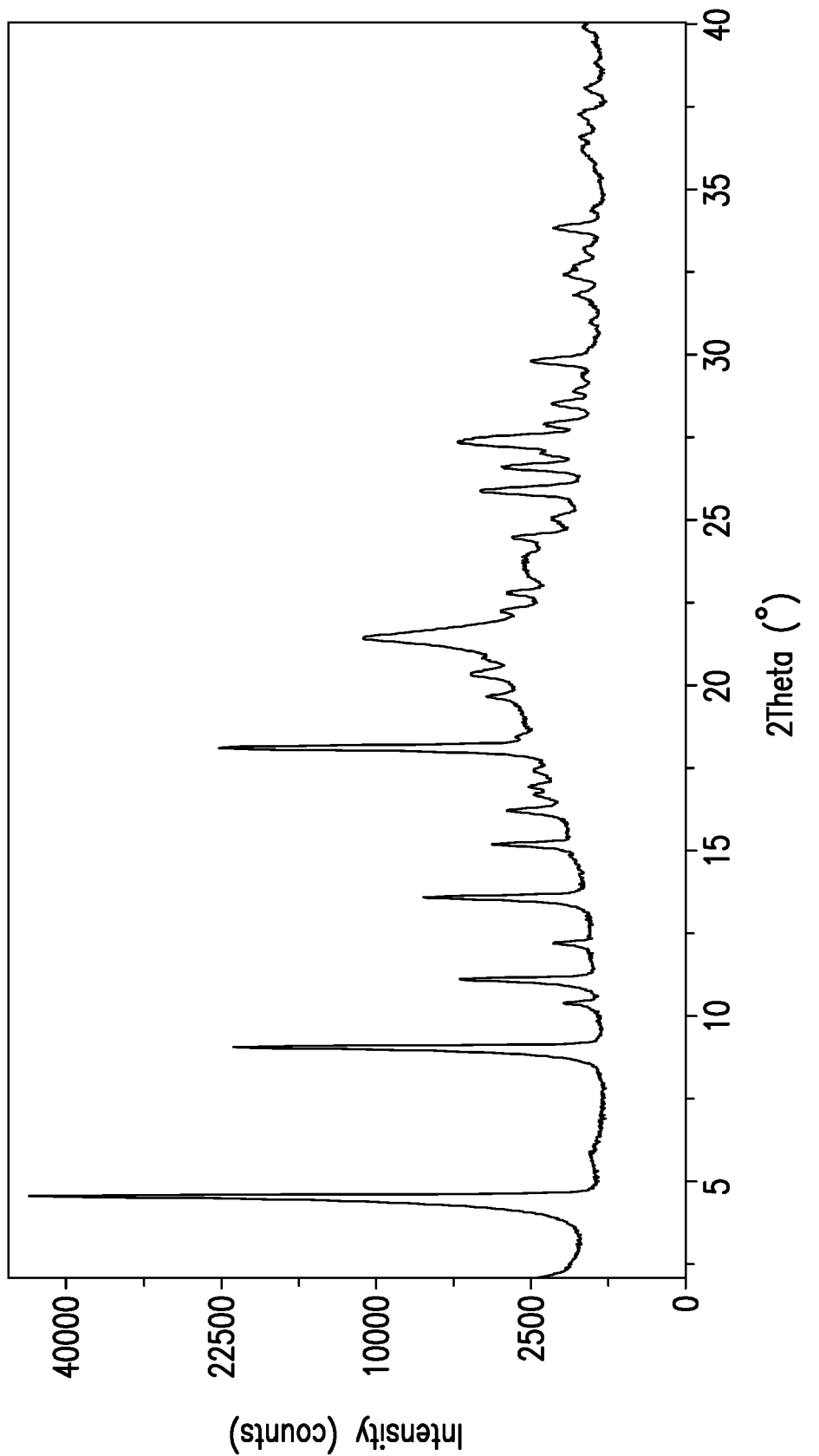
FIG. 13 is a graph of an X-Ray Diffraction ("XRD") pattern of a composition of monohydrate crystalline Form MH of EFdA and EVA polymer after undergoing hot melt extrusion processing with HME high shear Process B which resulted in conversion of Form MH to anhydrate crystalline Form 4 of EFdA in the composition.
Figure 14:
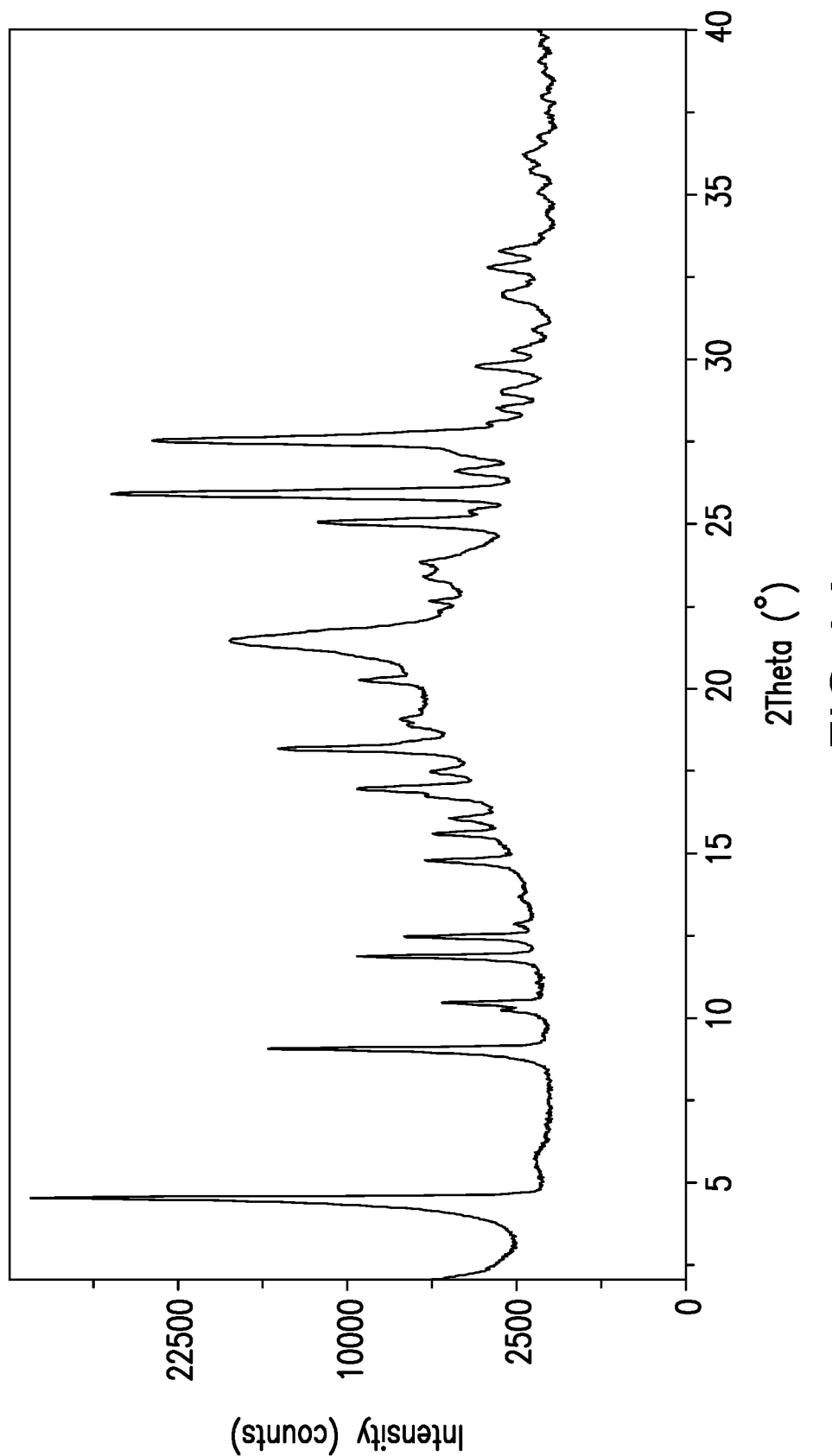
FIG. 14 is a graph of an X-Ray Diffraction ("XRD") pattern of a composition of anhydrate crystalline Form 1 of EFdA and EVA polymer after undergoing hot melt extrusion processing with HME low shear Process A which resulted in maintenance of anhydrate crystalline Form 1 of EFdA in the composition.
Figure 15:
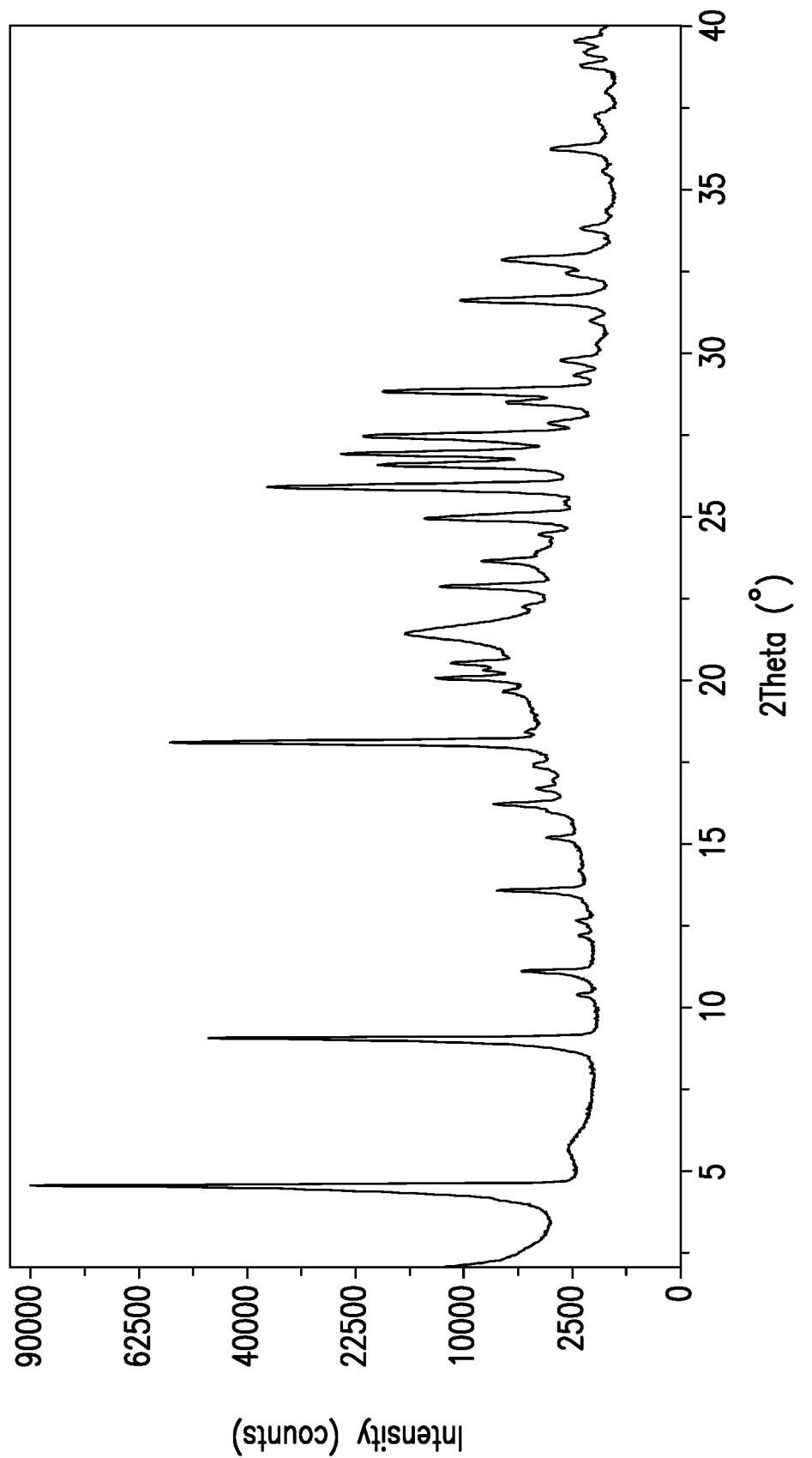
FIG. 15 is a graph of an X-Ray Diffraction ("XRD") pattern of a composition of anhydrate crystalline Form 4 of EFdA, EVA polymer and $BaSO_4$ after undergoing hot melt extrusion processing with HME low shear Process A which resulted in maintenance of anhydrate crystalline Form 4 of EFdA.

FIGS. 12-14 are PXRD patterns generated from LAP implant drug product compositions comprised of EFdA and EVA polymer ("EFdA/EVA product") prepared by HME. FIG. 12 demonstrates that the monohydrate Form MH is inadequate for implant HME manufacture, as it changes crystalline form in the process to the undesirable and thermodynamically disfavored Form 2. FIG. 13 demonstrates that Form 4 was generated by an unusual and unexpected mechanism, which involved the use of high shear forces in the HME process. FIG. 14 demonstrates the thermal stability of Form 1 in the HME process. FIG. 15 is a PXD pattern generated from LAP implant drug product compositions comprised of EFdA, EVA polymer and $BaSO_4$ ("EFdA/EVA/$BaSO_4$ product") prepared by HME. FIG. 15 demonstrates the thermal stability of Form 4 in the HME process, thereby achieving a long-acting implant EFdA product composed of a thermodynamically stable phase EFdA.

Example 1

The Gibbs free energy ($\Delta G$) of a phase is the fundamental thermodynamic parameter that determines the relative stability of a polymorphs at a given temperature. The solubility of a particular polymorph is related to the $\Delta G$ by the equation $\Delta G=-RT\ln$ (solubility). The polymorph with the lowest solubility is considered to be the thermodynamically stable phase at a given temperature. Table 6 lists the measured solubility for Forms 1, 2 and 4 of EFdA in acetonitrile between 25.0 and 65.0° C. The data clearly demonstrates that the most thermodynamically stable phase of EFdA over the measured temperature range is Form 4 with Form 2 being the least stable phase. The relatively low $\Delta\Delta G$ values for conversion of Form 1 to Form 4 (i.e., the energy gap between Form 1 and Form 4 is small; 0.21-0.35 kJ/mol), combined with the fast crystallization kinetics of Form 1 as compared to Form 4, result in difficulties isolating Form 4 using conventional methods of polymorph screening.

TABLE 6

Solubility of EFdA Forms 1, 2 and 4 in Acetonitrile as a Function of Temperature and Calculated ΔΔ Gibbs Free Energy (G) Between Form 1 and Form 4

| Temperature (° C.) | Solubility Form 1 (mg/g solv.) | Solubility Form 2 (mg/g solv.) | Solubility Form 4 (mg/g solv.) | Solubility Ratio (Form 1/4) | Form 1 and Form 4 ΔΔG (kJ/mol) |
|---|---|---|---|---|---|
| 25.0 | 2.15 ± 0.02 | 2.43 ± 0.01 | 1.87 ± 0.02 | 1.15 | 0.35 |
| 35.0 | 2.43 ± 0.01 | 3.20 ± 0.03 | 2.14 ± 0.02 | 1.13 | 0.33 |
| 45.0 | 3.44 ± 0.02 | 4.39 ± 0.04 | 3.18 ± 0.01 | 1.08 | 0.21 |
| 55.0 | 4.74 ± 0.02 | 5.79 ± 0.09 | 4.24 ± 0.01 | 1.12 | 0.30 |
| 65.0 | 6.81 ± 0.03 | 7.72 ± 0.12 | 6.05 ± 0.05 | 1.13 | 0.33 |

Figure 16:
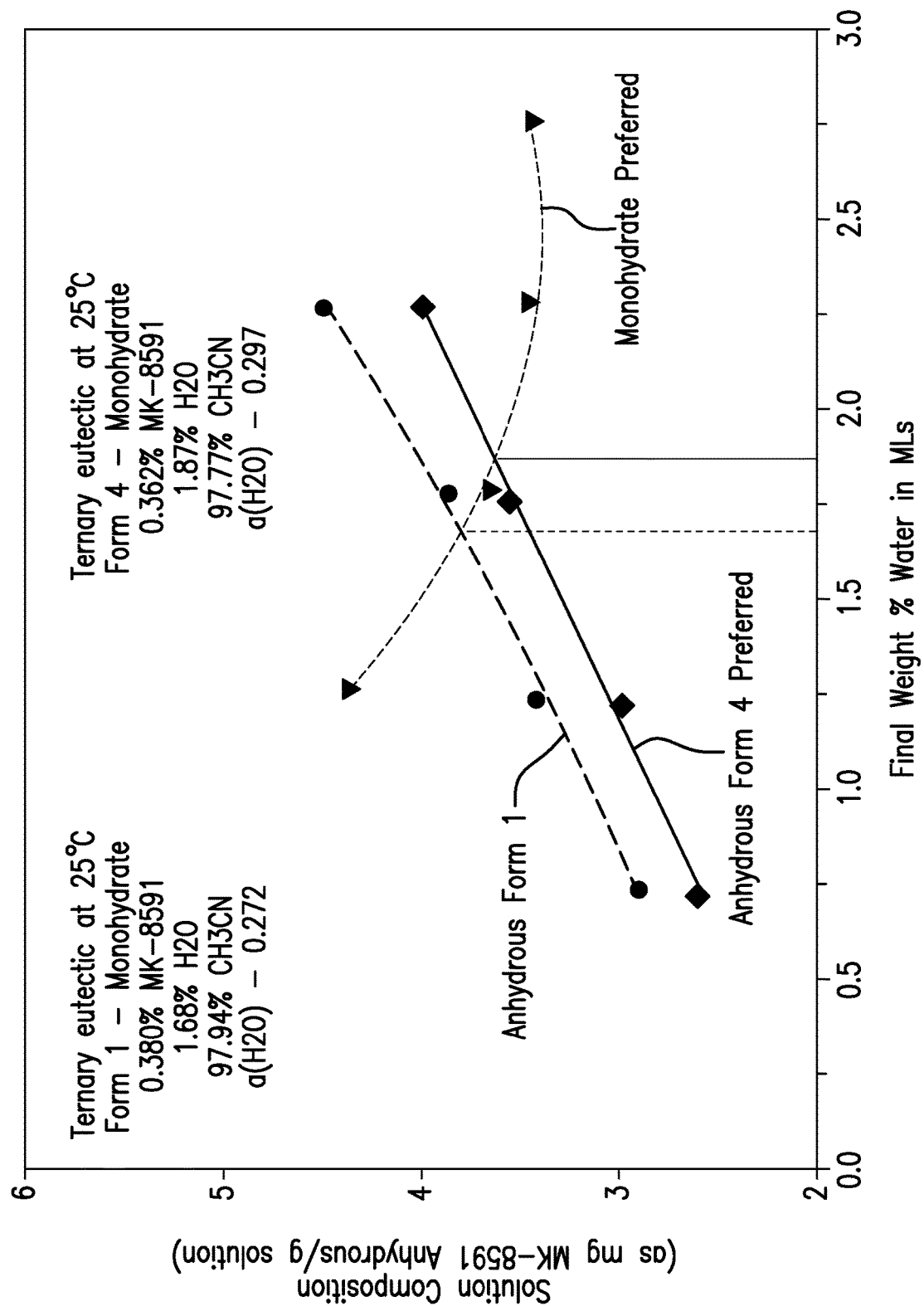
FIG. 16 is a graph depicting the solubility of anhydrate crystalline Forms 1, 2 and 4 of EFdA in acetonitrile as a function of temperature and calculated AA Gibbs Free Energy (G) between anhydrate crystalline Form 1 and Form 4 of EFdA.

The thermodynamic parameter for the stability of the monohydrate Form MH and anhydrate Form 4 of EFdA is the critical water activity. Below this water activity, anhydrous Form 4 is thermodynamically preferred. Above this water activity, monohydrate Form MH is thermodynamically preferred. The solubility of EFdA monohydrate Form MH and anhydrate Forms 1 and 4 were determined in acetonitrile as a function of water content at 25.0° C. A plot of the data is shown in FIG. 16. The critical water activity for the EFdA monohydrate/Form 4 system at 25° C. was determined to be 0.3.

Example 2: Monohydrate Crystalline Form MH of EFdA

Suitable starting quantities of Form MH of EFdA may be obtained by the synthetic process described in U.S. Pat. No. 7,339,053.

As those skilled in the art will appreciate, the use of seed crystal in the preparation of Form 1 and Form 4 as described in Examples 4 and 6 is not initially required but is used for optimal production after initial quantities of crystalline Form 1 and Form 4, respectively, are produced.

Example 3: Anhydrate Crystalline Form 1 of EFdA

EFdA Form 1 was prepared by adding 1.92 g of EFdA solid and 16.0 g of methanol (MeOH) to a clean reactor and heating to 65° C. while stirring. The mixture was cooled to 40° C. over 30 minutes, 20° C. over 1 hr and then stirred at 20° C. for ~14 hrs. The slurry was filtered and the cake was dried by passing $N_2$ through the cake at ambient temperature for 2 hrs. 1.59 g of EFdA Form 1 was collected in an ~88% isolated yield.

Example 4: Anhydrate Crystalline Form 1 of EFdA

EFdA Form 1 was prepared by dissolving 16.12 g of EFdA solid in dimethylformamide (DMF) with stirring for 30 minutes at ambient temperature. The resulting solution was filtered to remove undissolved matter and the filter was washed 2 times with ~1 ml of DMF and the filtrate and wash were combined. 294.4 g of Isopropanol (IPA) was added to a clean reactor and heated to 50° C. While stirring the IPA, 15.0 g of the EFdA/DMF solution was added to the IPA. The solution was seeded with 152 mg of EFdA Form 1 and stirred for 20 minutes. 10.56 g of the EFdA/DMF solution was added to the reactor and stirred for 20 minutes. 10.79 g of the EFdA/DMF solution was added to the reactor and stirred for 15 minutes. The slurry was stirred at 50° C. for 1 hr., cooled to 10° C. over 12 hrs, and stirred at 10° C. for 2.5 hrs. The slurry was filtered and the wet cake was washed 2 times with ~13 ml of IPA. The wet solid was dried at ambient temperature by passing $N_2$ through the cake for 3 hrs. 13.54 g of EFdA Form 1 was collected in an ~84% isolated yield.

Example 5: Anhydrate Crystalline Form 4 of EFdA

EFdA Form 4 was prepared by premixing 0.396 g of water ($H_2O$) with acetonitrile (MeCN) to a total solvent weight of 31.66 g. EFdA Form MH (monohydrate) (2.83 g) and 31.02 g of the MeCN/$H_2O$ solvent mixture was added to a clean reactor. The resulting slurry was stirred at 25° C. for 5 minutes and then heated to 35° C. over 30 minutes and then 40° C. over 30 minutes. After stirring at 40° C. for 45 minutes, the slurry was heated to 50° C. over 2 hrs and then stirred at 50° C. for 1 hr. After the 1 hr age at 50° C., the slurry was cooled to 25° C. over 8 hrs. The resulting slurry was filtered and dried by passing nitrogen ($N_2$) through the cake at ambient temperature for 24 hrs. 2.47 g of EFdA Form 4 was collected in a 93% isolated yield.

Example 6: Anhydrate Crystalline Form 4 of EFdA

EFdA Form 4 was prepared using the critical water activity data by exploiting the control of super-saturation by slowly heating a slurry of the monohydrate in a system with a water amount slight below the critical water activity. The Form 4 preparation was done by premixing 0.9134 g of water and 73.07 g of acetonitrile in a bottle. 60.03 g of the acetonitrile/water mixture and 7.82 g of EFDA monohydrate were added to a clean vessel. The suspension was stirred for 30 minutes at 25° C. Following a 30 minute age period, 0.80 g of EFDA Form 4 seed was added and the suspension was stirred for 30 minutes at 25.0° C. The suspension was heated to 55° C. linearly over 10 hrs. 42.5 ml of acetonitrile was added to the slurry linearly over 2 hrs while stirring at 55° C. At the end of the acetonitrile addition, the slurry was stirred for 1 hr at 55° C. The slurry was then cooled to 25.0° C. linearly over 4 hrs and stirred for an additional 2 hrs at 25° C. The slurry was filtered and washed with 20 ml of acetonitrile and dried by sucking nitrogen through the cake for 24 hrs at ambient temperature. EFDA Form 4 was collected (7.82 g) to give a 95% yield correcting for the seed.

Example 7

EFdA/EVA product was fabricated from Form MH of EFdA and EVA using HME low shear Process A. While fabricated from Form MH of EFdA starting material, the HME processing converted the Form MH phase into anhydrate Form 1 and anhydrate Form 2 in the drug product. FIG. 12 shows the XRD pattern of the resulting mixture of Form 1 and Form 2 of EFdA in this EFdA/EVA product. This result demonstrates the lack of stability of EFdA Form MH under the fabrication conditions that is needed for preparation of an EFdA/EVA implant product, and therefore the unsuitability of Form MH of EFdA for use in an implant product.

Example 8

EFdA/EVA product was fabricated from Form MH of EFdA and EVA using HME high shear Process B with processing at the limit of process parameter space. While fabricated from Form MH of EFdA starting material, the HME processing converted the Form MH phase into anhydrate Form 4. FIG. 13 shows the XRD pattern of the resulting Form 4 of EFdA in this EFdA/EVA product. This result demonstrates the unusual manner in which Form 4 was discovered. This likewise demonstrates the unsuitability of Form MH of EFdA for use in a hot melt extruded EFdA/EVA product due to its instability under the processing conditions.

Example 9

EFdA/EVA product was fabricated from Form 1 of EFdA and EVA using HME low shear Process A. Under the process conditions, EFdA Form 1 was maintained throughout the HME process into the EFdA/EVA product. FIG. 14 shows the XRD pattern of the resulting EFdA Form 1 in this EFdA/EVA product. This demonstrates that EFdA Form 1 is superior to EFdA Form MH due to the thermal stability of Form 1 in the HME process.

Example 10

EFdA/EVA product containing $BaSO_4$ was fabricated from Form 4 of EFdA and EVA using HME low shear Process A. Under the process conditions, EFdA Form 4 was maintained throughout the HME process into the EFdA/EVA product. FIG. 15 shows the XRD pattern of the resulting EFdA Form 4 in this EFdA/EVA product. This demonstrates that EFdA Form 4 is superior to EFdA Form MH due to the thermal stability of Form 4 in the HME process. This result also demonstrates the thermodynamic stability of Form 4 and also confirms the data shown in Example 1.

Properties: Crystalline Forms 1 and 4 of EFdA described and characterized herein exhibit excellent physical properties while minimizing the difficulties associated with drug product manufacturing and processing. For example, Crystalline Forms 1 and 4 of EFdA exhibit unexpectedly improved thermal stability in drug product (solid dosage long-acting parenteral implant) compared to monohydrate Form MH of EFdA while remaining a BCS Class I category substance. Despite its desirable properties, Crystalline Form 4 of EFdA did not appear during routine polymorph screening; it was surprisingly and advantageously invented after many batches of other crystalline forms (such as Monohydrate MH and Crystalline Anhydrous Form II) were produced using multiple synthetic routes in a variety of conditions at multiple manufacturing sites.

The thermodynamic stability of Crystalline Form 4 of EFdA was assessed using competitive slurry experiments in various solvent systems. Crystalline Forms 1 and 4 of EFdA, obtained as described above, were slurried in various solvents for an extended period of time and at a controlled temperature. At the end of the experiments, the solvent was removed and the remaining crystalline material were evaluated using Powder X-ray Diffraction (PXRD) to confirm the resultant form. Typically the more stable form will remain and the less stable form will convert to the more stable form. In all cases, Crystalline Form 4 of EFdA was the only form remaining and thus the more stable form.

Employing a novel crystalline form of EFdA according to the invention allows the use of formulation strategies for manufacture of long-acting parenteral formulations while maintaining the thermodynamically stable phase. This is significant in that Crystalline Form 4 of EFdA exhibits a reduced physical stability risk compared to higher energy state forms. Ultimately this may allow for less protective and potentially less expensive packaging configurations.

Pharmaceutical Compositions

As noted above, another embodiment provides a pharmaceutical composition comprising Crystalline Form 1 or Form #4 of EFdA (as characterized by any of the characterizations, alone or in combination, described herein). In such compositions, Crystalline Form 1 or Form 4 of EFdA comprises either the sole active agent, or is optionally present in combination with one or more additional therapeutic agents. In either case, said pharmaceutical compositions can further comprise one or more pharmaceutically acceptable carriers, excipients and/or diluents. Non-limiting examples of additional therapeutic agents which may be useful in combination with a Crystalline Form 1 or Form 4 of EFdA are described, for example, in PCT Publication WO 2017/196697 and include those selected from the group consisting of drugs for the treatment or prophylaxis of infection by HIV, and/or the treatment, prophylaxis, or delay in the onset of ARC or AIDS.

When used in combination with additional therapeutic agents, crystalline Form 1 or crystalline Form 4 of EFdA and the one or more additional agents may be administered together or sequentially, as noted above. When used contemporaneously with one or more other drugs, a pharmaceutical composition in unit dosage form containing such other drugs and crystalline Form 1 or crystalline Form 4 of EFdA is contemplated. However, the combination therapy may also include therapies in which crystalline Form 1 or crystalline Form 4 and one or more other drugs are administered on different overlapping schedules. It is also contemplated that when used in combination with one or more other active ingredients, crystalline Form 1 or crystalline Form 4 and the other active ingredient(s) may be used in lower doses than when each is used singly. Further, such other drugs may be administered by a route and in an amount commonly used therefor, contemporaneously or sequentially with crystalline Form 1 or crystalline Form 4. When crystalline Form 1 or crystalline Form 4 is used contemporaneously with one or more other drugs, a pharmaceutical composition comprising such other drugs in addition to crystalline Form 1 or crystalline Form 4 are prepared without undue experimentation in accordance with the methods described herein and/or known in the art.

The weight ratio of crystalline Form 1 or crystalline Form 4 to the second active ingredient may be varied and will depend upon the effective dose of each ingredient. Generally, an effective dose of each is used. Thus, for example, when crystalline Form 1 or crystalline Form 4 of EFdA is combined with another agent, the weight ratio of the crystalline Form 1 or crystalline Form 4 and the second agent will generally range from about 1000:1 to about 1:1000, such as about 200:1 to about 1:200, wherein, in each case an effective dose for the intended purpose is used. Such combinations may be administered separately or concurrently, and the administration of one may be prior to, concurrent with, or subsequent to the administration of the other agent(s).

For preparing the pharmaceutical compositions described herein, pharmaceutically acceptable carriers can be solid or liquid, or in any other known dosage form such as aerosols or lotions. Non-limiting examples of solid form preparations include powders, tablets, dispersible granules, capsules, cachets and suppositories. The powders and tablets may be comprised of any of the weight % values of active ingredient described herein, and in any desired dose (e.g., doses as described herein).

Crystalline Form 1 or crystalline Form 4 of EFdA may conveniently be presented in a dosage unit form which may be prepared by any of the methods well known in art of pharmacy. All methods include the step of bringing crystalline Form 1 or crystalline Form 4 into association with the carrier which constitutes accessory ingredients. In general, the pharmaceutical compositions are prepared by uniformly and intimately bringing active ingredient into association with a liquid carrier or finely divided solid carrier or both, and then, if necessary, shaping the product into the desired formulation.

In the pharmaceutical composition, the active ingredient(s) are included in an effective amount. The term "effective amount" as used herein means an amount of a compound sufficient to inhibit HIV reverse transcriptase, inhibit HIV replication, exert a prophylactic effect, and/or a exert a therapeutic effect after administration. One embodiment of "effective amount" is a "therapeutically effective amount" which is an amount of a compound that is effective for inhibiting HIV reverse transcriptase, inhibiting HIV replication (either of the foregoing which may also be referred to herein as an "inhibition effective amount"), treating HIV infection, treating AIDS, delaying the onset of AIDS, and/or slowing progression of ARC or AIDS in a patient infected with HIV. Another embodiment of "effective amount" is a "prophylactically effective amount" which is an amount of the compound that is effective for prophylaxis of HIV infection in a subject not infected with HIV, or prophylaxis of ARC or AIDS in an HIV-infected patient. It is understood that an effective amount can simultaneously be both a therapeutically effective amount, e.g., for treatment of HIV infection, and a prophylactically effective amount, e.g., for prevention or reduction of risk for developing AIDS in a subject infected with HIV. The term "preventing," as used herein with respect to an HIV viral infection or AIDS, refers to reducing the likelihood or severity of HIV infection or AIDS. When crystalline Form 1 or Form 4 of EFdA is administered as a salt, reference to an amount of the compound in milligrams or grams is based on the free form (i.e., the non-salt form) of the compound.

In the combination therapies of the present disclosure, an effective amount can refer to each individual agent or to the combination as a whole, wherein the amounts of all agents administered in the combination are together effective, but wherein a component agent of the combination may or may not be present individually in an effective amount with reference to what is considered effective for that component agent if it were administered alone.

Pharmaceutical compositions intended for parenteral use are contemplated herein, particularly a long-acting implantable drug delivery device adapted to provide an effective amount of crystalline Form 1 or crystalline Form 4 of EFdA over an extended period of time for example, but not limited to, over the course of a month, 3 months, 6 months or a year, or longer. Parenteral compositions can be prepared according to techniques known in the art and typically employ sterile water as a carrier and optionally other ingredients, such as a solubility aid.

Pharmaceutical compositions comprised of crystalline Form 1 or crystalline Form 4 of EFdA intended for oral use such as tablets or capsules may be prepared in accordance with methods described herein and other methods well known in the art for the manufacture of pharmaceutical compositions. Such compositions may further contain active agents selected from sweetening agents, flavoring agents, coloring agents and preserving agents where pharmaceutically elegant and/or palatable preparations are desired. Tablets or capsules may contain active ingredient in admixture with non-toxic pharmaceutically acceptable excipients which are suitable for the manufacture of tablets. Additional examples of dosage forms, formulations, and pharmaceutically acceptable carriers and methods of manufacture for various compositions may be found in Remington's Pharmaceutical Sciences, 18th edition, edited by A. R. Gennaro, Mack Publishing Co., 1990; and in Remington—The Science and Practice of Pharmacy, 22nd Edition, published by Pharmaceutical Press and Philadelphia College of Pharmacy at University of the Sciences, 2012, ISBN 978 0 85711-062-6 and prior editions.

Another embodiment provides suitable dosages and dosage forms of crystalline Form 1 or crystalline Form 4 of EFdA and use in the various methods described herein. Suitable doses for administering crystalline Form 1 or Form 4 to patients may readily be determined by those skilled in art, e.g., by an attending physician, pharmacist, or other skilled worker, and may vary according to patient health, age, weight, frequency, route of administration and/or duration of administration, use with other active ingredients, and/or indication for which crystalline Form 1 or crystalline Form 4 is administered. Thus, the dosage of active ingredient in the compositions of this invention may be varied, however, the amount of the active ingredient should be such that a suitable dosage form is obtained. The doses may be administered to patients in need of such treatment in dosages that will provide optimal pharmaceutical efficacy. Daily dosage amounts may range, for example, from about 0.01-10 mg per day by extended release from an implantable device over the course of a month, 3 months, 6 months, a year or longer, or from a daily dose of a tablet or capsule containing about 0.01-10 mg per day of crystalline Form 1 or crystalline Form 4.

What is claimed is:

1. Crystalline anhydrous Form 1 of 2' deoxy-4'-C-ethynyl-2-fluoroadenosine (EFdA) characterized by:
   (1) a powder x-ray diffraction pattern with peaks at diffraction angles degrees 2 theta (+/−) 0.2° of 4.48, 11.79, 14.70 and 25.81 in a powder x-ray diffraction obtained using Cu K alpha radiation, and/or
   (2) a solid state $^{19}$F NMR spectrum comprising any two of the following peaks: −114.75, −117.09 and −118.92 ppm.

2. The crystalline anhydrous Form 1 of EFdA according to claim 1, characterized by a powder x-ray diffraction pattern with peaks at diffraction angles degrees 2 theta (+/−) 0.2° of 4.48, 11.79, 14.70, 25.81, 8.99, 12.39, 16.88 and 27.42.

3. The crystalline anhydrous Form 1 of EFdA according to claim 1, characterized by a powder x-ray diffraction pattern with peaks at diffraction angles degrees 2 theta (+/−) 0.2° of 4.48, 11.79, 14.70, 25.81, 8.99, 12.39, 16.88, 27.42, 10.39, 15.51, 18.09 and 20.16.

4. Crystalline anhydrous Form 1 of EFdA according to claim 1 characterized by a solid state $^{19}$F NMR spectrum comprising the following peaks: −114.75, −117.09 and −118.92 ppm.

5. The crystalline anhydrous Form 1 of EFdA according to claim 1, characterized by a solid state $^{19}$F NMR spectrum comprising the following peaks: −117.09 and −118.92 ppm.

6. The crystalline anhydrous Form 1 of EFdA according to claim 1, further characterized by:
   (1) a TGA data showing 0.1 wt. % loss up to 133° C., followed by thermal decomposition above 240° C., or
   (2) a TGA curve as shown in FIG. 3.

7. Crystalline anhydrous Form 4 of 2' deoxy-4'-C-ethynyl-2-fluoroadenosine (EFdA) having the powder x-ray diffraction pattern as shown in FIG. 7.

8. The crystalline anhydrous Form 4 of EFdA of claim 7 further characterized by a solid state $^{19}$F NMR spectrum comprising peaks at −116.96 and −118.36 ppm.

9. The crystalline anhydrous Form 4 of EFdA according to claim 8, further characterized by:
   (1) TGA data showing 0.02 wt. % loss up to 148° C., followed by thermal decomposition above 250° C.; or
   (2) a TGA curve as shown in FIG. 9.

10. A solid dosage pharmaceutical composition comprising the crystalline anhydrate Form 1 of EFdA according to claim 1 and a pharmaceutically acceptable carrier.

11. A solid dosage pharmaceutical composition comprising the crystalline anhydrate Form 4 of EFdA according to claim 7 and a pharmaceutically acceptable carrier.

12. The pharmaceutical composition of claim 10, wherein the composition is adapted for long-acting parenteral administration.

13. The pharmaceutical composition of claim 11, wherein the composition is adapted for long-acting parenteral administration.

14. The crystalline anhydrous Form 1 of EFdA according to claim 1, characterized by a powder x-ray diffraction pattern comprising six or more of the 2-theta values listed in Table 1, +/−0.2° 2-theta.

15. The crystalline anhydrous Form 1 of EFdA according to claim 1, characterized by a powder x-ray diffraction pattern comprising nine or more of the 2-theta values listed in Table 1, +/−0.2° 2-theta.

16. The crystalline anhydrous Form 4 of EFdA according to claim 7, characterized by a powder x-ray diffraction pattern comprising six or more of the 2-theta values listed in Table 4, +/−0.2° 2-theta.

17. The crystalline anhydrous Form 4 of EFdA according to claim 1, characterized by a powder x-ray diffraction pattern comprising nine or more of the 2-theta values listed in Table 4, +/−0.2° 2-theta.

18. The crystalline anhydrous Form 4 of EFdA according to claim 7, characterized by a powder x-ray diffraction pattern with peaks at diffraction angles degrees 2 theta (+/−) 0.2° of 4.48, 11.79, 12.39, 14.70, 15.51, 18.09, 25.81, and 27.42.

* * * * *